(12) United States Patent
Janardhanan et al.

(10) Patent No.: US 11,628,172 B2
(45) Date of Patent: Apr. 18, 2023

(54) METHODS OF TREATING CHRONIC LYMPHOCYTIC LEUKEMIA USING 2-(2,6-DIOXOPIPERIDIN-3-YL)-4-((2-FLUORO-4-((3-MORPHOLINOAZETIDIN-1-YL)METHYL)BENZYL)AMINO) ISOINDOLINE-1,3-DIONE

(71) Applicant: Celgene Corporation, Summit, NJ (US)

(72) Inventors: Preethi Janardhanan, San Diego, CA (US); Shailaja Kasibhatla, San Diego, CA (US); Antonia Lopez-Girona, San Diego, CA (US); Michael Pourdehnad, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 56 days.

(21) Appl. No.: 17/075,125

(22) Filed: Oct. 20, 2020

(65) Prior Publication Data

US 2021/0113574 A1 Apr. 22, 2021

Related U.S. Application Data

(60) Provisional application No. 63/011,147, filed on Apr. 16, 2020, provisional application No. 62/923,955, filed on Oct. 21, 2019.

(51) Int. Cl.
| | | |
|---|---|---|
| *A61K 31/5377* | (2006.01) | |
| *A61P 35/02* | (2006.01) | |
| *A61K 9/00* | (2006.01) | |
| *C07K 16/28* | (2006.01) | |
| *A61K 39/00* | (2006.01) | |

(52) U.S. Cl.
CPC ........ *A61K 31/5377* (2013.01); *A61K 9/0053* (2013.01); *A61P 35/02* (2018.01); *C07K 16/2887* (2013.01); *A61K 2039/505* (2013.01); *A61K 2039/545* (2013.01)

(58) Field of Classification Search
CPC .................................................. A61K 31/5377
See application file for complete search history.

(56) References Cited

U.S. PATENT DOCUMENTS

2016/0045484 A1   2/2016   Tun

FOREIGN PATENT DOCUMENTS

| WO | WO 2008/033567 | 3/2008 |
|---|---|---|
| WO | WO 2016/007854 | 1/2016 |
| WO | WO 2019/209692 A1 | 10/2019 |
| WO | WO 2020/210418 A1 | 10/2020 |

OTHER PUBLICATIONS

Potapov, V.M., 1988 "Stereochemistry: Textbook for Higher Education, the 2nd revised edition" Moscow—Chemistry (464 pages), specifically pp. 416-417.
Cartron, G. et al, 2017 "Obinutuzumab: what is there to learn from clinical trials" Blood 130(5):581-589.
Marcus, R. et al, 2017 "Obinutuzumab for the First-Line Treatment of Follicular Lymphoma" N Engl J Med 2017; 377:1331-1344.

*Primary Examiner* — Rei Tsang Shiao
(74) *Attorney, Agent, or Firm* — Jones Day

(57) ABSTRACT

Provided herein are methods of using 2-(2,6-dioxopiperidin-3-yl)-4-((2-fluoro-4-((3-morpholinoazetidin-1-yl)methyl) benzyl)amino)isoindoline-1,3-dione, or an enantiomer, a mixture of enantiomers, a tautomer, an isotopolog, or a pharmaceutically acceptable salt thereof, alone or in combination with obinutuzumab, for treating, preventing or managing chronic lymphocytic leukemia/small lymphocytic lymphoma.

25 Claims, 2 Drawing Sheets

METHODS OF TREATING CHRONIC LYMPHOCYTIC LEUKEMIA USING 2-(2,6-DIOXOPIPERIDIN-3-YL)-4-((2-FLUORO-4-((3-MORPHOLINOAZETIDIN-1-YL)METHYL)BENZYL)AMINO) ISOINDOLINE-1,3-DIONE

This application claims priority to U.S. Provisional Application No. 62/923,955, filed on Oct. 21, 2019, and U.S. Provisional Application No. 63/011,147, filed on Apr. 16, 2020, the entirety of each of which is incorporated herein by reference.

FIELD

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with obinutuzumab, for treating, preventing or managing chronic lymphocytic leukemia/small lymphocytic lymphoma (CLL/SLL).

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in *Nature Reviews Clinical Oncology* 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

Despite availability of a variety of chemotherapeutic agents, chemotherapy has many drawbacks. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Chronic lymphocytic leukemia (CLL) is a lymphoproliferative malignancy characterized by the progressive accumulation of morphologically mature but functionally incompetent B lymphocytes in the blood, bone marrow, and lymphoid tissues with a unique cluster of differentiation (CD) CD19+, CD5+, and CD23+ phenotype. It is the most common leukemia in North America and Europe with an incidence of 4.0 cases per 100,000 persons per year that affects mainly elderly patients with the median age at presentation of 72 years. The clinical course of CLL ranges from indolent disease with long-term survival over 12 years to aggressive disease with median survival of 2 years and is influenced by stage at presentation and certain disease-specific characteristics such as cytogenetic abnormalities. Current clinical course and prognosis reflect an evolving therapeutic landscape including emerging newer agents becoming available for the treatment of CLL. Despite the recent introduction of several highly effective agents CLL remains an incurable disease for patients who do not undergo allogeneic stem cell transplantation and therefore warrants development of alternative and additional treatment options.

The molecular pathogenesis of CLL/SLL is a complex, multi-faceted process characterized by specific genetic aberrations and represents the convergence of alterations in cell signaling pathways including the B-cell receptor and apoptotic pathways, and the influence of the tumor-immune microenvironment. The term CLL is used when the disease manifests primarily in the blood, whereas the term small lymphocytic lymphoma (SLL) is used when involvement is primarily nodal. Specifically, SLL as defined by the International Workshop on Chronic Lymphocytic Leukemia (iwCLL) criteria, is a disease in patients who would otherwise be diagnosed as CLL, but which presents with a relatively normal peripheral lymphocyte count, and which requires the presence of lymphadenopathy and/or splenomegaly. In contrast to CLL, which is often found in the blood and bone marrow, as well as other disease locations, such as lymph nodes, spleen and extranodal locations, patients with SLL have less prominent manifestations in the peripheral blood.

As evidenced by recent regulatory approvals of several new targeted agents such as ibrutinib and venetoclax, the CLL treatment landscape is evolving. However, despite the availability of these newer agents, patients continue to relapse or are refractory to treatment. Moreover, patients with poor risk cytogenetic features continue to have worse outcomes compared with patients without these characteristics. Improved and novel combination treatments for CLL will remain an important medical need. In addition, the increased use of targeted therapies has triggered the emergence of novel mutations that have been shown to confer resistance to therapy. For example, resistance to the BTK inhibitor ibrutinib has been associated with mutations either in the BTK binding site or mutations that resulted in autonomous B-cell receptor activity. Therefore, exploration of agents with novel mechanisms is important to offer treatment options with unique mechanism of actions (MOAs) for patients who may develop resistance to emerging targeted agents.

Citation or identification of any reference in this section of this application is not to be construed as an admission that the reference is prior art to the present application.

SUMMARY

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with obinutuzumab, for treating, preventing or managing CLL/SLL.

In certain embodiments, provided herein is a method of treating CLL/SLL, comprising administering to a subject in need thereof a therapeutically effective amount of Compound 1 of the formula:

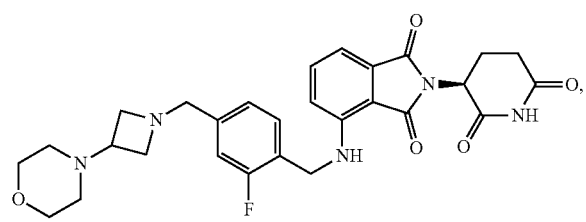

1 or a tautomer, isotopolog, or pharmaceutically acceptable salt thereof.

In certain embodiments, provided herein is a method of treating CLL/SLL, comprising administering to a subject in need thereof a therapeutically effective amount of Compound 2 of the formula:

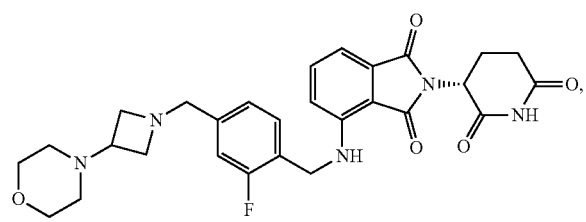

2 or a tautomer, isotopolog, or pharmaceutically acceptable salt thereof.

In certain embodiments, provided herein is a method of treating CLL/SLL, comprising administering to a subject in need thereof a therapeutically effective amount of Compound 3 of the formula:

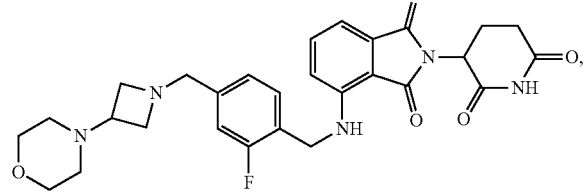

3 or an enantiomer, mixture of enantiomers, tautomer, isotopolog, or pharmaceutically acceptable salt thereof.

In certain embodiments, provided herein is a compound for use in method of treating chronic lymphocytic leukemia/small lymphocytic lymphoma (CLL/SLL), wherein the compound is Compound 3 of the formula:

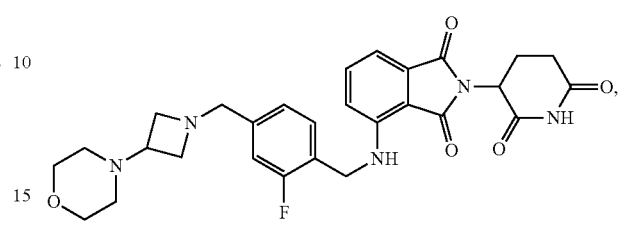

3 or an enantiomer, mixture of enantiomers, tautomer, isotopolog, or pharmaceutically acceptable salt thereof, wherein the method comprises administering to a subject in need thereof a therapeutically effective amount of the compound.

In certain embodiments, provided herein is a compound for use in method of treating chronic lymphocytic leukemia/small lymphocytic lymphoma (CLL/SLL), wherein the compound is Compound 1 of the formula:

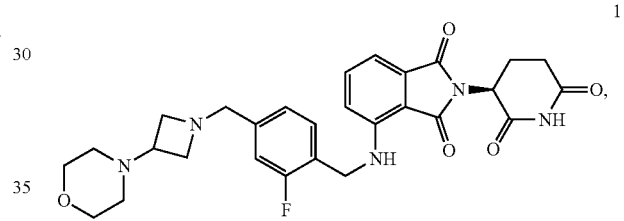

1 or a tautomer, isotopolog, or pharmaceutically acceptable salt thereof, wherein the method comprises administering to a subject in need thereof a therapeutically effective amount of the compound.

In certain embodiments, provided herein is a compound for use in method of treating chronic lymphocytic leukemia/small lymphocytic lymphoma (CLL/SLL), wherein the compound is Compound 2 of the formula:

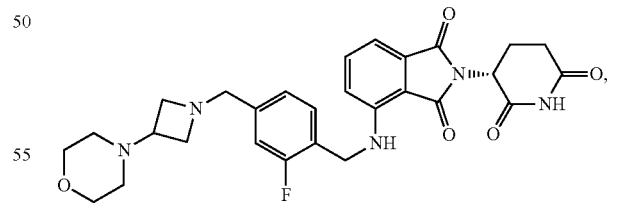

2 or a tautomer, isotopolog, or pharmaceutically acceptable salt thereof, wherein the method comprises administering to a subject in need thereof a therapeutically effective amount of the compound.

In certain embodiments, the CLL/SLL is relapsed or refractory CLL/SLL.

In certain embodiments, the methods provided herein further comprising administering to the subject a therapeutically effective amount of obinutuzumab.

The present embodiments can be understood more fully by reference to the detailed description and examples, which are intended to exemplify non-limiting embodiments.

DETAILED DESCRIPTION

Definitions

Figure 1:
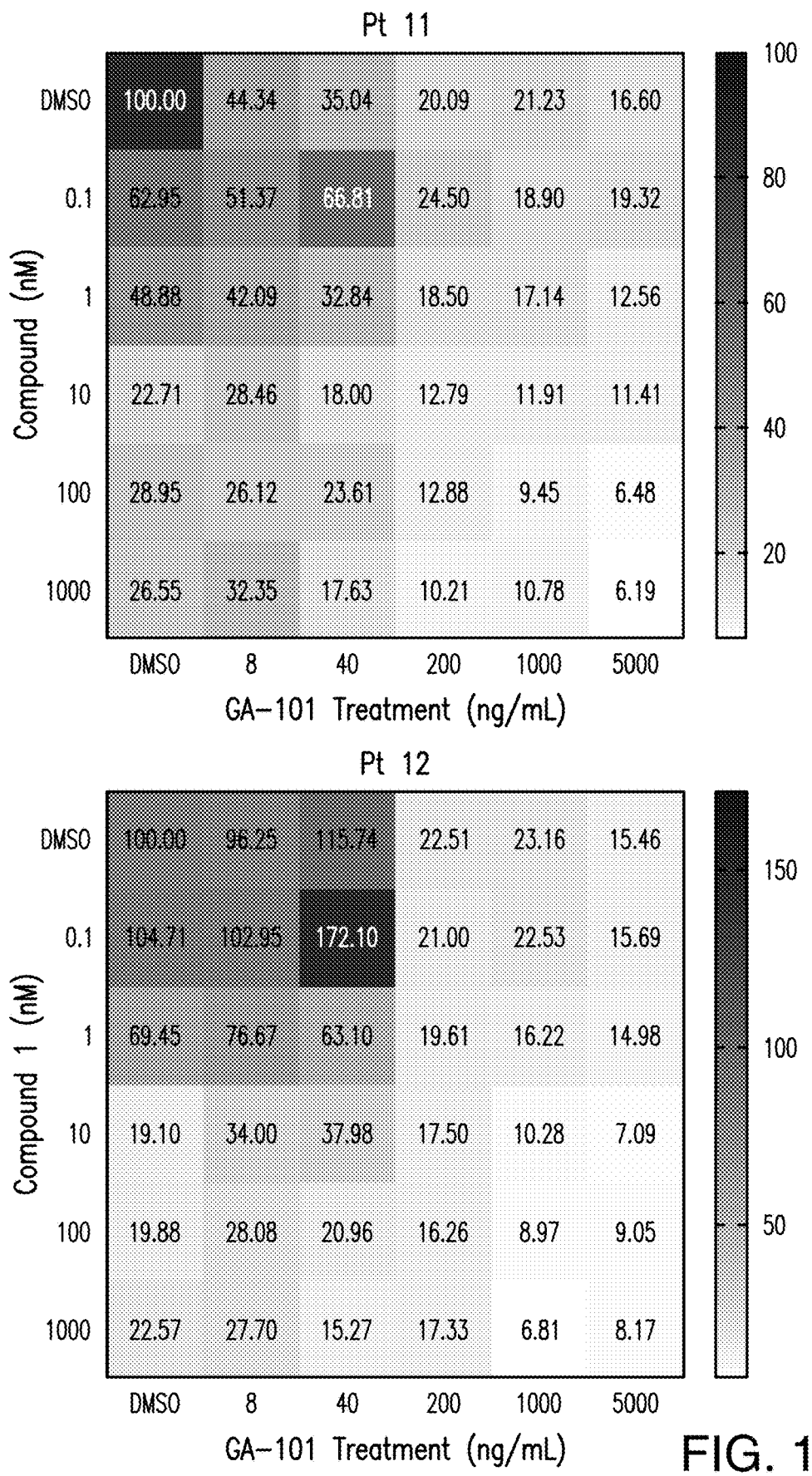
FIG. 1 illustrates heat map of normalized percentage of tumor cells after treatment with Compound 1 in combination with obinutuzumab.
Figure 1:
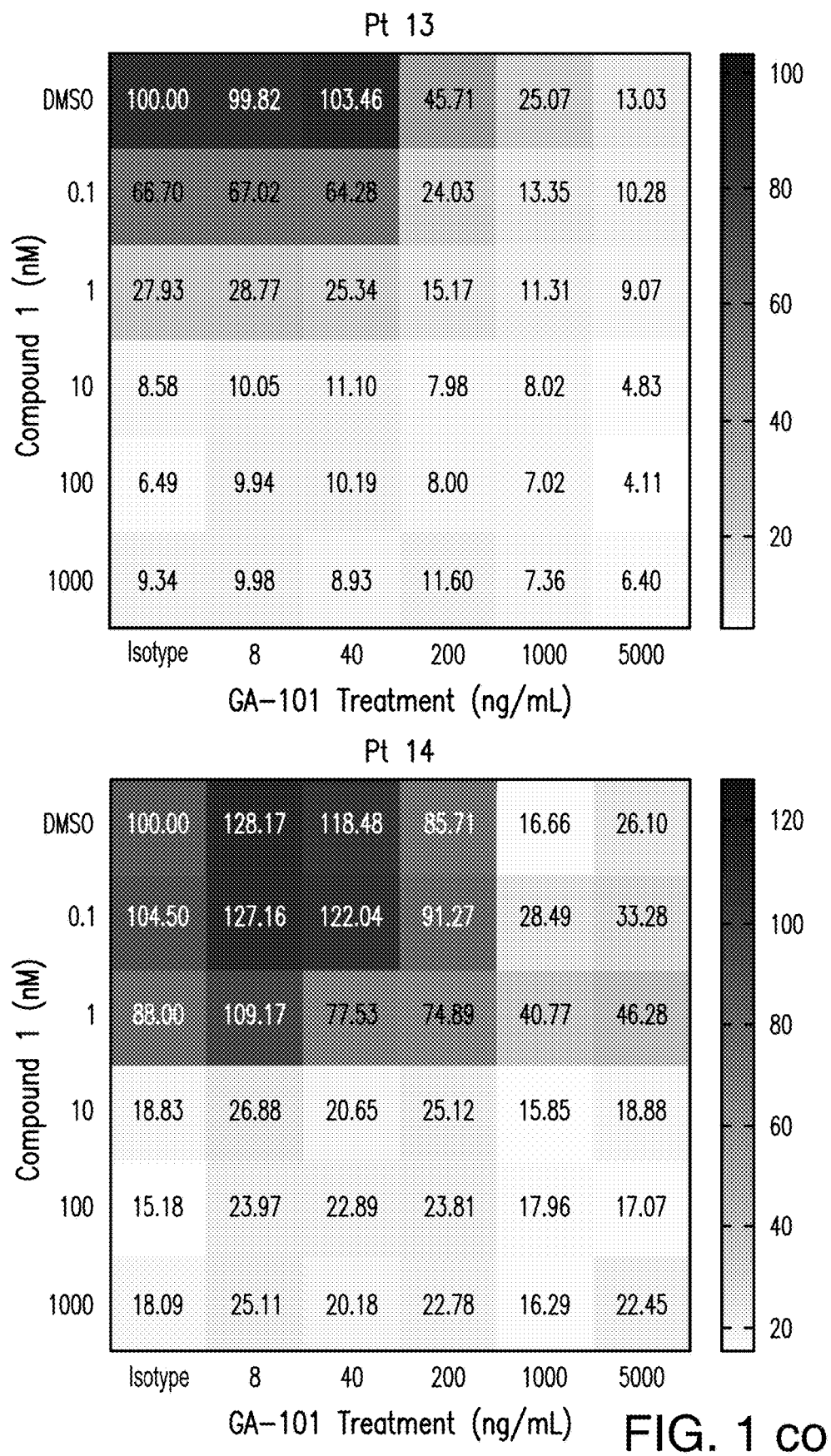

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of a compound provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereoisomerically pure" means one stereoisomer of a compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments provided herein, including mixtures thereof.

The use of stereoisomerically pure forms of such compounds, as well as the use of mixtures of those forms, are encompassed by the embodiments provided herein. For example, mixtures comprising equal or unequal amounts of the enantiomers of a particular compound may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. *L., Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

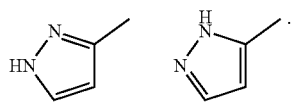

As readily understood by one skilled in the art, a wide variety of functional groups and other structures may exhibit tautomerism and all tautomers of a compound are within the scope of the compound as provided herein.

It should also be noted that a compound provided herein can contain unnatural proportions of atomic isotopes at one or more of the atoms. For example, the compounds may be radiolabeled with radioactive isotopes, such as for example tritium ($^3H$), iodine-125 ($^{125}I$) sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of a compound, whether radioactive or not, are intended to be encompassed within the scope of the compound as provided herein. In some embodiments, provided herein are isotopologs of the compounds, for example, the isotopologs are deuterium, carbon-13 ($^{13}C$), and/or nitrogen-15 ($^{15}N$) enriched compounds. As used herein, "deuterated", means a compound wherein at least one hydrogen (H) has been replaced by deuterium (indicated by D or $^2H$), that is, the compound is enriched in deuterium in at least one position.

It is understood that, independently of stereoisomerical or isotopic composition, each compound provided herein can be provided in the form of any of the pharmaceutically acceptable salts provided herein. Equally, it is understood that the isotopic composition may vary independently from the stereoisomerical composition of each compound provided herein. Further, the isotopic composition, while being restricted to those elements present in the respective compound or salt thereof, may otherwise vary independently from the selection of the pharmaceutically acceptable salt of the respective compound.

It should be noted that if there is a discrepancy between a depicted structure and a name for that structure, the depicted structure is to be accorded more weight.

As used herein and unless otherwise indicated, the term "treating" means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein and unless otherwise indicated, the term "preventing" means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein and unless otherwise indicated, the term "effective amount" in connection with a compound means an amount capable of treating, preventing, or managing a disorder, disease or condition, or symptoms thereof.

As used herein and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

As used herein and unless otherwise indicated, the term "relapsed" refers to a disorder, disease, or condition that responded to treatment (e.g., achieved a complete response) then had progression. The treatment can include one or more lines of therapy. In one embodiment, the disorder, disease or condition has been previously treated with one or more lines of therapy. In another embodiment, the disorder, disease or condition has been previously treated with one, two, three or four lines of therapy.

As used herein and unless otherwise indicated, the term "refractory" refers to a disorder, disease, or condition that has not responded to prior treatment that can include one or more lines of therapy. In one embodiment, the disorder, disease, or condition has been previously treated one, two, three or four lines of therapy. In one embodiment, the disorder, disease, or condition has been previously treated with two or more lines of treatment, and has less than a complete response (CR) to most recent systemic therapy containing regimen.

In one embodiment, "relapsed or refractory" CLL/SLL may refer to CLL/SLL that has been previously treated with one or more lines of therapy. In one embodiment, the relapsed or refractory CLL/SLL is CLL/SLL that has been previously treated with one, two, three or four lines of therapy. In one embodiment, the relapsed or refractory CLL/SLL is CLL/SLL that has been previously treated with two or more lines of therapy. In one embodiment, the relapsed or refractory CLL/SLL is CLL/SLL that has been previously treated with an inhibitor of B-cell receptor signaling. In one embodiment, the relapsed or refractory CLL/SLL is relapsed or refractory to an inhibitor of B-cell receptor signaling. In one embodiment, the relapsed or refractory CLL/SLL is CLL/SLL that has been previously treated with a Bruton's tyrosine kinase (BTK) inhibitor. In one embodiment, the relapsed or refractory CLL/SLL is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib. In one embodiment, the relapsed or refractory CLL/SLL is CLL/SLL that has been previously treated with a phosphoinositide 3-kinase (PI3K) inhibitor. In one embodiment, the relapsed or refractory CLL/SLL is relapsed or refractory to a PI3K inhibitor. In one embodiment, the PI3K inhibitor is duvelisib. In one embodiment, the PI3K inhibitor is idelalisib. In one embodiment, the relapsed or refractory CLL/SLL is CLL/SLL that has been previously treated with venetoclax. In one embodiment, the relapsed or refractory CLL/SLL is relapsed or refractory to venetoclax. In one embodiment, the relapsed or refractory CLL/SLL is CLL/SLL that has been previously treated with obinutuzumab. In one embodiment, the relapsed or refractory CLL/SLL is relapsed or refractory to obinutuzumab.

In the context of a cancer, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates are computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR). In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In one embodiment, the treatment response of CLL/SLL may be assessed by the International Workshop on Chronic Lymphocytic Leukemia criteria (see Hallek, M, et al. iwCLL guidelines for diagnosis, indications for treatment, response assessment, and supportive management of CLL. *Blood,* 131(25), 2745-2760 (2018)) (Table 1). In one embodiment, the treatment response of CLL/SLL may be assessed by the International Workshop Lyphoma Response Criteria (see Cheson B D, Fisher R I, Barrington S F, Cavalli F, Schwartz L H, Zucca E, et al. Recommendations for initial evaluation, staging, and response assessment of Hodgkin and non-Hodgkin lymphoma: the Lugano classification. J Clin Oncol. 2014; 32(27):3059-3068) (Table 1a).

TABLE 1

Response Definition after Treatment for Chronic Lymphocytic Leukemia Patients.

| Group | Parameter | CR | PR | PD | SD |
|---|---|---|---|---|---|
| A | Lymph nodes | None > 1.5 cm | Decrease ≥50% (from the baseline)[a] | Increase ≥50% from baseline or from response | Change of −49% to +49% |
| | Liver and/or spleen size[b] | Spleen size, <13 cm; liver size normal | Decrease ≥50% (from the baseline) | Increase ≥50% from baseline or from response | Change of −49% to +49% |
| | Constitutional symptoms | None | Any | Any | Any |
| | Circulating lymphocyte count | Normal | Decrease ≥50% from baseline | Increase ≥50% over baseline | Change of −49% to +49% |
| B | Platelet count | ≥100 × 10⁹/L | ≥100 × 10⁹/L or increase ≥50% over baseline | Decrease of ≥50% from baseline secondary to CLL | Change of −49% to +49% |
| | Hemoglobin | ≥11.0 g/dL (untransfused and without erythropoietin) | ≥11.0 g/dL or increase ≥50% over baseline | Decrease of >2 g/dL from baseline secondary to CLL | Increase, 11.0 g/dL or <50% over baseline, or decrease <2 g/dL |

TABLE 1-continued

Response Definition after Treatment for Chronic Lymphocytic Leukemia Patients.

| Group | Parameter | CR | PR | PD | SD |
|---|---|---|---|---|---|
| | Marrow | Normocellular, no CLL cells, no B-lymphoid nodules | Presence of CLL cells, or of B-lymphoid nodules, or not done | Increase of CLL cells by ≥50% on successive biopsies | No change in marrow infiltrate |

CR = complete remission (all of the criteria have to be met);
PD = progressive disease (at least 1 of the criteria of group A or group B has to be met);
PR = partial remission (for a PR, at least 2 of the parameters of group A and 1 parameter of group B need to improve if previously abnormal; if only 1 parameter of both groups A and B is abnormal before therapy, only 1 needs to improve);
SD = stable disease (all of the criteria have to be met; constitutional symptoms alone do not define PD).
[a]Sum of the products of 6 or fewer lymph nodes (as evaluated by CT scans and physical examination in clinical trials or by physical examination in general practice).
[b]Spleen size is considered normal if, <13 cm. There is not firmly established international consensus of the size of a normal liver; therefore, liver size should be evaluated by imaging and manual palpation in clinical trials and be recorded according to the definition used in a study protocol.

TABLE 1a

Summary of Revised Criteria for Response Assessment

| Response Category | PET-CT-Based Response | CT-Based Response |
|---|---|---|
| CR | Complete metabolic response Score 1, 2, or 3 with or without a residual mass on 5PS A complete metabolic response even with a persistent mass is considered a complete remission | Target nodes/nodal masses must regress to ≤1.5 cm in longest diameter No extralymphatic sites of disease |
| PR | Partial metabolic response Score 4 or 5 with reduced uptake compared with baseline and residual masses of any size | All of the following: ≥50% decrease in SPD of up to 6 target measurable nodes and extranodal sites Spleen must have regressed by >50% in length beyond normal |
| SD | No metabolic response Score 4 or 5 with no significant change in FDG uptake from baseline | <50% decrease from baseline in SPD of up to 6 dominant, measurable nodes and extranodal sites No criteria for PD are met |
| PD | Progressive metabolic disease Score 4 or 5 with an increase in intensity of uptake from baseline and/or New FDG-avid foci consistent with lymphoma Bone marrow: New or recurrent FDG-avid foci | At least 1 of the following: An individual node/lesion must be abnormal with: Longest diameter >1.5 cm and increase by ≥50% from nadir and An increase by longest diameter or shortest diameter from nadir In the setting of splenomegaly, the splenic length must increase by >50% of the extent of its prior increase beyond baseline New or recurrent splenomegaly New or clear progression of preexisting nonmeasured lesions Regrowth of previously resolved lesions Bone marrow: New or recurrent involvement |

Abbreviations:
5PS: 5-point scale;
CR = complete response;
CT = computed tomography;
FDG = fluorodeoxyglucose;
PET = positron emission tomography;
PR = partial response;
PD = progressive disease;
SD = stable disease;
SPD = sum of the product of the perpendicular diameters for multiple lesions.

In one embodiment, the treatment response of CLL/SLL may be assessed by the Eastern Cooperative Oncology Group (ECOG) performance status (Table 2).

TABLE 2

ECOG Performance Status.

| Grade | ECOG |
|---|---|
| 0 | Fully active, able to carry on all pre-disease performance without restriction. |
| 1 | Restricted in physically strenuous activity but ambulatory and able to carry out work of a light or sedentary nature, e.g., light house work, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |
| 5 | Dead. |

ECOG = Eastern Cooperative Oncology Group, Robert Comis, MD, Group Chair.
Source: Oken M, et at. Toxicity and response criteria of the Eastern Cooperative Oncology Group. Am J Clin Oncol, 5(6): 649-655 (1982).

In certain embodiments, stable disease or lack thereof can be determined by methods known in the art such as evaluation of patient symptoms, physical examination, visualization of the tumor that has been imaged, for example using FDG-PET (fluorodeoxyglucose positron emission tomography), PET/CT (positron emission tomography/computed tomography) scan, MRI (magnetic resonance imaging) of the brain and spine, CSF (cerebrospinal fluid), ophthalmologic exams, vitreal fluid sampling, retinal photograph, bone marrow evaluation and other commonly accepted evaluation modalities.

As used herein and unless otherwise indicated, the terms "co-administration" and "in combination with" include the administration of one or more therapeutic agents (for example, a compound provided herein and another anti-CLL/SLL agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with another therapeutic agent.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In one embodiment, the terms "about" and "approximately," when used in this context, contemplate a dose, amount, or weight percent within 30%, within 20%, within 15%, within 10%, or within 5%, of the specified dose, amount, or weight percent.

Compounds

Provided for use in the methods provided herein is the compound (S)-2-(2,6-dioxopiperidin-3-yl)-4-((2-fluoro-4-((3-morpholinoazetidin-1-yl)methyl)benzyl)amino)isoindoline-1,3-dione, referred to as "Compound 1":

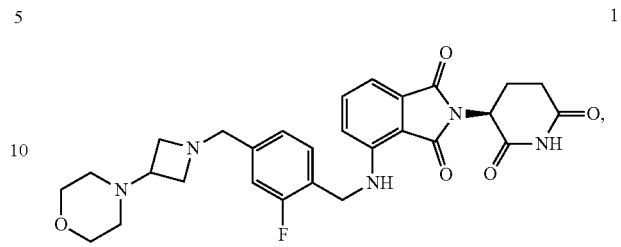

or a tautomer, isotopolog, or pharmaceutically acceptable salt thereof. Provided herein is Compound 1 for use in the methods of treatment provided herein.

Also provided for use in the methods provided herein is the compound (R)-2-(2,6-dioxopiperidin-3-yl)-4-((2-fluoro-4-((3-morpholinoazetidin-1-yl)methyl)benzyl)amino)isoindoline-1,3-dione, referred to as "Compound 2":

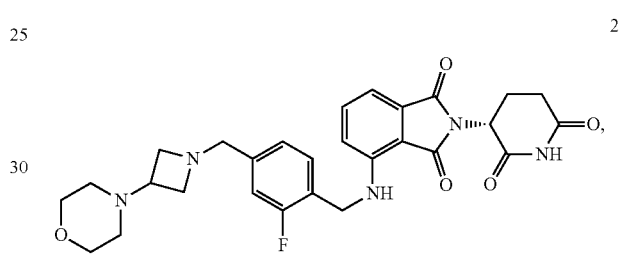

or a tautomer, isotopolog, or pharmaceutically acceptable salt thereof. Provided herein is Compound 2 for use in the methods of treatment provided herein.

Provided for use in the methods provided herein is the compound 2-(2,6-dioxopiperidin-3-yl)-4-((2-fluoro-4-((3-morpholinoazetidin-1-yl)methyl)benzyl)amino)isoindoline-1,3-dione, referred to as "Compound 3":

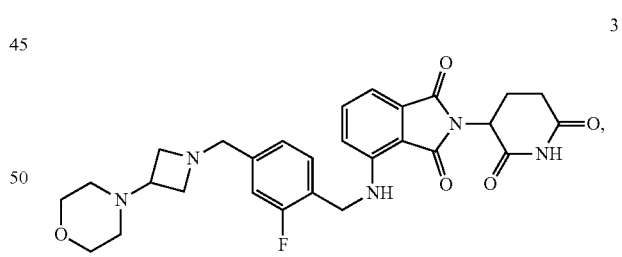

or an enantiomer, mixture of enantiomers, tautomer, isotopolog, or pharmaceutically acceptable salt thereof. Provided herein is Compound 3 for use in the methods of treatment provided herein.

In one embodiment, Compound 1 is used in the methods provided herein. In one embodiment, a tautomer of Compound 1 is used in the methods provided herein. In one embodiment, an isotopolog of Compound 1 is used in the methods provided herein. In one embodiment, a pharmaceutically acceptable salt of Compound 1 is used in the methods provided herein.

In one embodiment, Compound 2 is used in the methods provided herein. In one embodiment, a tautomer of Compound 2 is used in the methods provided herein. In one embodiment, an isotopolog of Compound 2 is used in the methods provided herein. In one embodiment, a pharmaceutically acceptable salt of Compound 2 is used in the methods provided herein.

In one embodiment, Compound 3 is used in the methods provided herein. In one embodiment, an enantiomer of Compound 3 is used in the methods provided herein. In one embodiment, a mixture of enantiomers of Compound 3 is used in the methods provided herein. In one embodiment, a tautomer of Compound 3 is used in the methods provided herein. In one embodiment, an isotopolog of Compound 3 is used in the methods provided herein. In one embodiment, a pharmaceutically acceptable salt of Compound 3 is used in the methods provided herein.

Methods of Treatment and Prevention

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, alone or in combination with obinutuzumab, for treating, preventing or managing CLL/SLL.

As used herein and unless otherwise indicated, "CLL/SLL" or "CLL and/or SLL" means CLL, or SLL, or CLL and SLL. In one embodiment, the methods provided herein are for treating, preventing or managing CLL. In one embodiment, the methods provided herein are for treating, preventing or managing SLL. In one embodiment, the methods provided herein are for treating, preventing or managing CLL and CLL.

In one embodiment, provided herein is a method of treating CLL/SLL, comprising administering to a subject in need thereof a therapeutically effective amount of Compound 1 of the formula:

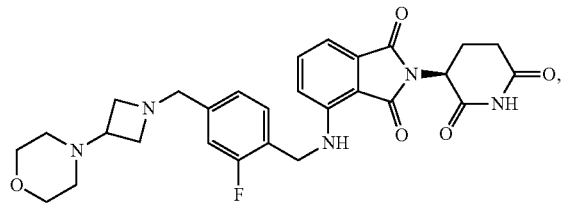

1 or a tautomer, isotopolog, or pharmaceutically acceptable salt thereof.

In one embodiment, provided herein is a method of treating CLL/SLL, comprising administering to a subject in need thereof a therapeutically effective amount of Compound 2 of the formula:

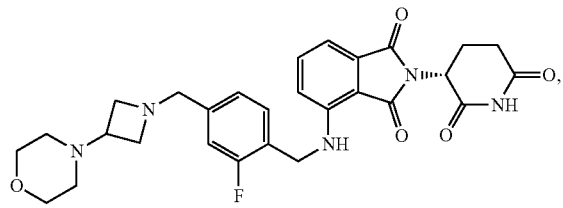

2 or a tautomer, isotopolog, or pharmaceutically acceptable salt thereof.

In one embodiment, provided herein is a method of treating CLL/SLL, comprising administering to a subject in need thereof a therapeutically effective amount of Compound 3 of the formula:

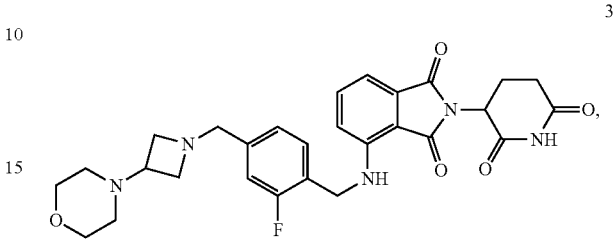

3 or an enantiomer, mixture of enantiomers, tautomer, isotopolog, or pharmaceutically acceptable salt thereof.

In one embodiment, provided herein is a method of preventing CLL/SLL, which comprises administering to a subject in need thereof a therapeutically effective amount of Compound 1, or a tautomer, isotopolog, or pharmaceutically acceptable salt thereof. In one embodiment, provided herein is a method of preventing CLL/SLL, which comprises administering to a subject in need thereof a therapeutically effective amount of Compound 2, or a tautomer, isotopolog, or pharmaceutically acceptable salt thereof. In one embodiment, provided herein is a method of preventing CLL/SLL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing CLL/SLL, which comprises administering to a subject in need thereof a therapeutically effective amount of Compound 1, or a tautomer, isotopolog, or pharmaceutically acceptable salt thereof. In one embodiment, provided herein is a method of managing CLL/SLL, which comprises administering to a subject in need thereof a therapeutically effective amount of Compound 2, or a tautomer, isotopolog, or pharmaceutically acceptable salt thereof. In one embodiment, provided herein is a method of managing CLL/SLL, which comprises administering to a subject in need thereof a therapeutically effective amount of Compound 3, or an enantiomer, mixture of enantiomers, tautomer, isotopolog, or pharmaceutically acceptable salt thereof.

In one embodiment, the CLL/SLL subject has failed one or more lines of therapy. In one embodiment, the subject has failed at least one prior therapy. In one embodiment, the subject has failed at least two prior therapies. In one embodiment, the subject has been previously treated with an inhibitor of B-cell receptor signaling. In one embodiment, the subject is relapsed or refractory to an inhibitor of B-cell receptor signaling. In one embodiment, the subject has been previously treated with a Bruton's tyrosine kinase (BTK) inhibitor. In one embodiment, the subject is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib. In one embodiment, the subject has been previously treated with a phosphoinositide 3-kinase (PI3K) inhibitor. In one embodiment, the subject is relapsed or refractory to a PI3K inhibitor. In one embodiment, the PI3K inhibitor is duvelisib. In one embodiment, the PI3K inhibitor is idelalisib. In one embodiment, the subject has been previously treated with venetoclax. In one embodiment, the subject is relapsed or refractory to venetoclax. In one embodiment, the subject has been previously treated with obinutuzumab. In one embodiment, the subject is relapsed or refractory to obinutuzumab.

In one embodiment, the CLL/SLL is newly diagnosed CLL/SLL. In one embodiment, the CLL/SLL is relapsed or refractory CLL/SLL (R/R CLL/SLL).

In one embodiment, the CLL is characterized by mutated IGHV (Immunoglobulin Heavy Chain Gene). In one embodiment, the CLL is characterized by non-mutated IGHV.

In one embodiment, the CLL is characterized by one or more mutations in TP53 (Tumor Protein 53). In one embodiment, the CLL is characterized by wild type TP53.

In one embodiment, the CLL is characterized by one or more cytogenetic abnormalities, e.g., del(13q), del(11q), del(17p), tri12, t(6;17), del(11q22.3), t(11;14), del(18q), and t(14;19). In one embodiment, the CLL is characterized by del(17p).

In one embodiment, the CLL is characterized by Richter's Transformation (also known as Richter's Syndrome).

In one embodiment, the methods provided herein further comprise administering to the subject a therapeutically effective amount of obinutuzumab.

In one embodiment, a first therapy (e.g., an agent such as Compound 1, Compound 2 or Compound 3, or an enantiomer, mixture of enantiomers, tautomer, isotopolog, or pharmaceutically acceptable salt thereof) provided herein is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 120 hours, 144 hours, 1 week, 2 weeks, 3 weeks, 4 weeks, 5 weeks, 6 weeks, 8 weeks, or 12 weeks before) to the administration of a second therapy (e.g., obinutuzumab) to the subject.

In one embodiment, a first therapy (e.g., an agent such as Compound 1, Compound 2 or Compound 3, or an enantiomer, mixture of enantiomers, tautomer, isotopolog, or pharmaceutically acceptable salt thereof) provided herein is administered concomitantly with the administration of a second therapy (e.g., obinutuzumab) to the subject.

In one embodiment, a first therapy (e.g., an agent such as Compound 1, Compound 2 or Compound 3, or an enantiomer, mixture of enantiomers, tautomer, isotopolog, or pharmaceutically acceptable salt thereof) provided herein is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 120 hours, 144 hours, 1 week, 2 weeks, 3 weeks, 4 weeks, 5 weeks, 6 weeks, 8 weeks, or 12 weeks after) the administration of a second therapy (e.g., obinutuzumab) to the subject.

In one embodiment, a compound described herein, e.g., Compound 1, Compound 2 or Compound 3, or an enantiomer, mixture of enantiomers, tautomer, isotopolog, or pharmaceutically acceptable salt thereof, is administered at a dose of from about 0.1 mg to about 1.6 mg per day. In one embodiment, the compound is administered at a dose of from about 0.1 mg to about 1.2 mg per day. In one embodiment, the compound is administered at a dose of from about 0.1 mg to about 0.8 mg per day. In one embodiment, the compound is administered at a dose of from about 0.1 mg to about 0.6 mg per day. In one embodiment, the compound is administered at a dose of from about 0.1 mg to about 0.4 mg per day. In one embodiment, the compound is administered at a dose of from about 0.1 mg to about 0.2 mg per day. In one embodiment, the compound is administered at a dose of from about 0.2 mg to about 1.6 mg per day. In one embodiment, the compound is administered at a dose of from about 0.2 mg to about 1.2 mg per day. In one embodiment, the compound is administered at a dose of from about 0.2 mg to about 0.8 mg per day. In one embodiment, the compound is administered at a dose of from about 0.2 mg to about 0.6 mg per day. In one embodiment, the compound is administered at a dose of from about 0.2 mg to about 0.4 mg per day. In one embodiment, the compound is administered at a dose of from about 0.4 mg to about 1.6 mg per day. In one embodiment, the compound is administered at a dose of from about 0.4 mg to about 1.2 mg per day. In one embodiment, the compound is administered at a dose of from about 0.4 mg to about 0.8 mg per day. In one embodiment, the compound is administered at a dose of from about 0.4 mg to about 0.6 mg per day. In one embodiment, the compound is administered at a dose of from about 0.6 mg to about 1.6 mg per day. In one embodiment, the compound is administered at a dose of from about 0.6 mg to about 1.2 mg per day. In one embodiment, the compound is administered at a dose of from about 0.6 mg to about 0.8 mg per day. In one embodiment, the compound is administered at a dose of from about 0.8 mg to about 1.6 mg per day. In one embodiment, the compound is administered at a dose of from about 0.8 mg to about 1.2 mg per day. In one embodiment, the compound is administered at a dose of from about 1.2 mg to about 1.6 mg per day.

In certain embodiments, a compound described herein, e.g., Compound 1, Compound 2 or Compound 3, or an enantiomer, mixture of enantiomers, tautomer, isotopolog, or pharmaceutically acceptable salt thereof, is administered at a dose of about 0.1 mg, about 0.2 mg, about 0.4 mg, about 0.6 mg, about 0.8 mg, about 1.2 mg, or about 1.6 mg per day. In certain embodiments, the compound is administered at a dose of about 0.1 mg per day. In certain embodiments, the compound is administered at a dose of about 0.2 mg per day. In certain embodiments, the compound is administered at a dose of about 0.4 mg per day. In certain embodiments, the compound is administered at a dose of about 0.6 mg per day. In certain embodiments, the compound is administered at a dose of about 0.8 mg per day. In certain embodiments, the compound is administered at a dose of about 1.2 mg per day. In certain embodiments, the compound is administered at a dose of about 1.6 mg per day.

In one embodiment, obinutuzumab is administered according to the locally approved label or pharmacy manual for preparation, administration, and storage information. In one embodiment, obinutuzumab is administered intravenously. In one embodiment, obinutuzumab is administered subcutaneously. In one embodiment, obinutuzumab is administered via intravenous (IV) injection or IV infusion. In one embodiment, obinutuzumab is administered via IV injection. In one embodiment, obinutuzumab is administered via IV infusion.

In one embodiment, obinutuzumab is administered at an amount according to the physician's decision. In one embodiment, obinutuzumab is administered per day. In one embodiment, obinutuzumab is administered at a dose of from about 75 mg to about 1100 mg per day. In one embodiment, obinutuzumab is administered at a dose of from about 75 mg to about 125 mg per day, from about 800 mg to about 1000 mg per day, or from about 900 mg to about 1100 mg per day. In one embodiment, obinutuzumab is administered at a dose of about 100 mg per day. In one embodiment, obinutuzumab is administered at a dose of about 900 mg per day. In one embodiment, obinutuzumab is administered at a dose of about 1000 mg per day. In one embodiment, obinutuzumab is administered at a dose of about 100 mg on day 1 of a first 28-day cycle, about 900 mg on day 2 of the first 28-day cycle, and about 1000 mg on each of days 8 and 15 of the first 28-day cycle and day 1 of a second to a sixth 28-day cycles. In one embodiment, obinutuzumab is administered at a dose of about 1000 mg combined on day 1 and 2 of the first 28-day cycle, and about 1000 mg on each of days 8 and 15 of the first 28-day cycle and day 1 of a second to a sixth 28-day cycles. Obinutuzumab can be administered beyond six cycles. In one embodiment, obinutuzumab is administered in a first 28-day cycle as described herein, and is administered at about 1000 mg on day 1 of a second to a 12th 28-day cycles. In one embodiment, obinutuzumab is administered in a first 28-day cycle as described herein, and is administered at about 1000 mg on day 1 of a second to a 24th 28-day cycles. In one embodiment, obinutuzumab is administered in a first 28-day cycle as described herein, and is administered at about 1000 mg on day 1 of subsequent 28-day cycles until progression of disease.

In one embodiment, provided herein is a method of treating newly diagnosed CLL/SLL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of obinutuzumab.

In one embodiment, provided herein is a method of treating newly diagnosed CLL/SLL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of obinutuzumab.

In one embodiment, provided herein is a method of treating newly diagnosed CLL/SLL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of obinutuzumab.

In one embodiment, provided herein is a method of preventing newly diagnosed CLL/SLL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of obinutuzumab.

In another embodiment, provided herein is a method of managing newly diagnosed CLL/SLL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of obinutuzumab.

In one embodiment, provided herein is a method of treating relapsed or refractory CLL/SLL, which comprises administering to a subject in need thereof a therapeutically effective amount of Compound 1, or a tautomer, isotopolog, or pharmaceutically acceptable salt thereof. In one embodiment, the method further comprises administering to the subject a therapeutically effective amount of obinutuzumab.

In one embodiment, provided herein is a method of treating relapsed or refractory CLL/SLL, which comprises administering to a subject in need thereof a therapeutically effective amount of Compound 2, or a tautomer, isotopolog, or pharmaceutically acceptable salt thereof. In one embodiment, the method further comprises administering to the subject a therapeutically effective amount of obinutuzumab.

In one embodiment, provided herein is a method of treating relapsed or refractory CLL, which comprises administering to a subject in need thereof a therapeutically effective amount of Compound 3, or an enantiomer, mixture of enantiomers, tautomer, isotopolog, or pharmaceutically acceptable salt thereof. In one embodiment, the method further comprises administering to the subject a therapeutically effective amount of obinutuzumab.

In one embodiment, provided herein is a method of preventing relapsed or refractory CLL/SLL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of obinutuzumab.

In another embodiment, provided herein is a method of managing relapsed or refractory CLL/SLL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, the method further comprises administering to the subject a therapeutically effective amount of obinutuzumab.

In another embodiment, provided herein are methods for achieving a complete response, partial response, or stable disease, as determined by the International Workshop on Chronic Lymphocytic Leukemia criteria in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having CLL/SLL. In one embodiment, the methods further comprise administering to the subject a therapeutically effective amount of obinutuzumab.

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old.

Pharmaceutical Compositions and Routes of Administration

The compound provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as a diluent (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrant (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinyl pyrrolliclone or aluminum stearate), a dispersing agent (e.g., hydroxypropylmethylcellulose), water, and base wax (e.g., cocoa butter, white petrolatum or polyethylene glycol). The effective amount of the compounds in the pharmaceutical composition may be at a level that will exercise the desired effect for both oral and parenteral administration.

A compound provided herein can be administered orally. In one embodiment, when administered orally, a compound provided herein is administered with a meal and water. In another embodiment, the compound provided herein is dispersed in water or juice (e.g., apple juice or orange juice) and administered orally as a solution or a suspension.

The compound provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound provided herein without an additional excipient. In another embodiment, provided herein are compositions comprising an effective amount of a compound provided herein and a pharmaceutically acceptable excipient, wherein a pharmaceutically acceptable excipient can comprise a diluent, binder, disintegrant, glidant, lubricant, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a compound provided herein with a suitable excipient and filling the proper amount of the mixture in capsules. The usual excipients include, but are not limited to, inert powdered substances such as starch of many different kinds, powdered cellulose, especially crystalline and microcrystalline cellulose, sugars such as fructose, mannitol and sucrose, grain flours and similar edible powders. Capsules fill can also be prepared by wet granulation or by dry granulation.

A lubricant might be necessary in a capsule formulation to prevent the powder from sticking to the pin. The lubricant can be chosen from such slippery solids as talc, magnesium and calcium stearate, sodium stearyl fumarate, stearic acid and hydrogenated vegetable oils. Disintegrants are substances that swell when wetted to break up the capsule slug and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate.

Tablets can be prepared by direct compression, by wet granulation, or by dry granulation. Their formulations usually incorporate diluents, binders, lubricants and disintegrants as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, sodium stearyl fumarate, stearic acid and hydrogenated vegetable oils. Tablet disintegrants are substances that swell when wetted to break up the tablet and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound provided herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound provided herein can be delayed or prolonged by proper formulation. For example, a slowly soluble pellet of the compound provided herein can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound provided herein in oily or emulsified vehicles that allow it to disperse slowly in the serum.

Depending on the state of the disease to be treated and the subject's condition, Compound 1, Compound 2 or Compound 3 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral capsules, tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity.

Compound 1, Compound 2 or Compound 3 provided herein, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period.

In some embodiments, the frequency of administration is in the range of about a daily dose to about a monthly dose. In one embodiment, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In one embodiment, the methods provided herein include an administration of a therapeutically effective amount of Compound 1, Compound 2 or Compound 3 in one or more 7-day treatment cycles. In another embodiment, the methods provided herein include an administration of a therapeutically effective amount of Compound 1, Compound 2 or Compound 3 on days 1 to 5 of a 7-day cycle. In another embodiment, the methods provided herein include an administration of a therapeutically effective amount of Compound 1, Compound 2 or Compound 3 on days 1 to 3 of a 7-day cycle.

In one embodiment, the methods provided herein include an administration of a therapeutically effective amount of Compound 1, Compound 2 or Compound 3 in one or more 14-day treatment cycles. In another embodiment, the methods provided herein include an administration of a therapeutically effective amount of Compound 1, Compound 2 or Compound 3 on days 1 to 7 of a 14-day cycle. In another embodiment, the methods provided herein include an administration of a therapeutically effective amount of Compound 1, Compound 2 or Compound 3 on days 1 to 10 of a 14-day cycle. In another embodiment, the methods provided herein include an administration of a therapeutically effective amount of Compound 1, Compound 2 or Compound 3 on days 1 to 5 of a 14-day cycle.

In one embodiment, the methods provided herein include an administration of a therapeutically effective amount of Compound 1, Compound 2 or Compound 3 in one or more 28-day treatment cycles. In another embodiment, the methods provided herein include an administration of a therapeutically effective amount of Compound 1, Compound 2 or Compound 3 on days 1 to 21 of a 28-day cycle. In another embodiment, the methods provided herein include an administration of a therapeutically effective amount of Compound 1, Compound 2 or Compound 3 on days 1 to 5, days 8 to 12, days 15 to 19, and days 22 to 26 of a 28-day cycle. In another embodiment, the methods provided herein include an administration of a therapeutically effective amount of Compound 1, Compound 2 or Compound 3 on days 1 to 10 and days 15 to 24 of a 28-day cycle. In another embodiment, the methods provided herein include an administration of a therapeutically effective amount of Compound 1, Compound 2 or Compound 3 on days 1 to 7 and days 15 to 21 of a 28-day cycle. In another embodiment, the methods provided herein include an administration of a therapeutically effective amount of Compound 1, Compound 2 or Compound 3 on days 1 to 14 of a 28-day cycle.

In one embodiment, Compound 1, Compound 2 or Compound 3 is administered once daily for 5 days followed by 2 days of rest. In one embodiment, Compound 1, Compound 2 or Compound 3 is administered once daily for 3 days followed by 4 days of rest. In one embodiment, Compound 1, Compound 2 or Compound 3 is administered once daily for 5 days followed by 9 days of rest. In one embodiment, Compound 1, Compound 2 or Compound 3 is administered once daily for 7 days followed by 7 days of rest. In one embodiment, Compound 1, Compound 2 or Compound 3 is administered once daily for 10 days followed by 4 days of rest. In one embodiment, Compound 1, Compound 2 or Compound 3 is administered once daily for 21 days followed by 7 days of rest. In one embodiment, Compound 1, Compound 2 or Compound 3 is administered once daily for 14 days followed by 14 days of rest.

In one embodiment, the treatment includes an administration of a therapeutically effective amount of obinutuzumab in one or more treatment cycles. In one embodiment, obinutuzumab is administered twice every 7 days. In one embodiment, obinutuzumab is administered once every week. In one embodiment, obinutuzumab is administered once every 4 weeks. In one embodiment, obinutuzumab is administered on days 1, 2, 8, and 15 of the first 28-day cycle, and administered on day 1 of the second to the sixth 28-day cycles. In one embodiment, obinutuzumab is administered on day 1 of a second to a 12th 28-day cycles. In one embodiment, obinutuzumab is administered on day 1 of a second to a 24th 28-day cycles. In one embodiment, obinutuzumab is administered on day 1 of subsequent 28-day cycles until progression of disease.

In one embodiment, obinutuzumab is administered at a dose of about 100 mg on day 1 of the first 28-day cycle, about 900 mg on day 2 of the first 28-day cycle, and about 1000 mg on each of days 8 and 15 of the first 28-day cycle. In one embodiment, obinutuzumab is administered at a dose of about 1000 mg combined on day 1 and 2 of the first 28-day cycle, and about 1000 mg on each of days 8 and 15 of the first 28-day cycle. In one embodiment, obinutuzumab is administered at a dose of about 1000 mg on day 1 of the second to the sixth 28-day cycles. In one embodiment, obinutuzumab is administered at about 1000 mg on day 1 of a second to a 12th 28-day cycles. In one embodiment, obinutuzumab is administered at about 1000 mg on day 1 of a second to a 24th 28-day cycles. In one embodiment, obinutuzumab is administered at about 1000 mg on day 1 of subsequent 28-day cycles until progression of disease. In one embodiment, obinutuzumab is administered at a dose of about 1000 mg in the first 28-day cycle at least one week before initiating the administration of a compound provided herein, e.g., Compound 1.

In one embodiment, the subject receives an initial dose of obinutuzumab at least one week before receiving an initial dose of Compound 1. In one embodiment, the subject receives an initial dose of obinutuzumab one week before receiving an initial dose of Compound 1. In one embodiment, the subject receives an initial dose of obinutuzumab 13 days before receiving an initial dose of Compound 1. In one embodiment, the subject receives an initial dose of obinutuzumab 14 days before receiving an initial dose of Compound 1. In one embodiment, the subject receives an initial dose of obinutuzumab 14 days before receiving an initial dose of Compound 1 and receives subsequent doses of obinutuzumab 13 days and 7 days before receiving the initial dose of Compound 1. In one embodiment, the initial dose of obinutuzumab is at least 1000 mg. In one embodiment, the initial dose of obinutuzumab is about 1000 mg. The initial dose of obinutuzumab can be a single dose administered in one day, or combined doses administered in more than one day. In one embodiment, the subject receives obinutuzumab at a dose of about 100 mg on day 1 of the first 28-day cycle, about 900 mg on day 2 of the first 28-day cycle, and about 1000 mg on day 8 the first 28-day cycle, before receiving an initial dose of Compound 1 on day 15 of the first 28-day cycle. In one embodiment, the subject receives obinutuzumab at a dose of about 1000 mg combined on days 1 and 2 of the first 28-day cycle, and about 1000 mg on day 8 the first 28-day cycle, before receiving an initial dose of Compound 1 on day 15 of the first 28-day cycle.

In one embodiment, the method provided herein comprises administering an initial dose of obinutuzumab at least one week before administering an initial dose of Compound 1. In one embodiment, the method provided herein comprises administering an initial dose of obinutuzumab one week before administering an initial dose of Compound 1. In one embodiment, the method provided herein comprises administering an initial dose of obinutuzumab 13 days before administering an initial dose of Compound 1. In one embodiment, the method provided herein comprises administering an initial dose of obinutuzumab 14 days before administering an initial dose of Compound 1. In one embodiment, the method provided herein comprises administering an initial dose of obinutuzumab 14 days before administering an initial dose of Compound 1 and administering subsequent doses of obinutuzumab 13 days and 7 days before administering the initial dose of Compound 1. In one embodiment, the initial dose of obinutuzumab is at least 1000 mg. In one embodiment, the initial dose of obinutuzumab is about 1000 mg. The initial dose of obinutuzumab can be a single dose administered in one day, or combined doses administered in more than one day. In one embodiment, the method provided herein comprises administering obinutuzumab at a dose of about 100 mg on day 1 of the first 28-day cycle, about 900 mg on day 2 of the first 28-day cycle, and about 1000 mg on day 8 the first 28-day cycle, before administering an initial dose of Compound 1 on day 15 of the first 28-day cycle. In one embodiment, the method provided herein comprises administering obinutuzumab at a dose of about 1000 mg combined on days 1 and 2 of the first 28-day cycle, and about 1000 mg on day 8 the first 28-day cycle, before administering an initial dose of Compound 1 on day 15 of the first 28-day cycle.

In one embodiment, the method provided herein comprises (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s) ("Cycle 2" and so on); and (ii) administering Compound 1 in cycles of once daily for 7 days followed by 7 days of rest, starting on day 15 of Cycle 1.

In one embodiment, the method provided herein comprises (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s) ("Cycle 2" and so on); and (ii) administering Compound 1 in cycles of once daily for 5 days followed by 9 days of rest, starting on day 15 of Cycle 1.

In one embodiment, the method provided herein comprises (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s) ("Cycle 2" and so on); and (ii) administering Compound 1 in cycles of once daily for 14 days followed by 14 days of rest, starting on day 15 of Cycle 1.

In one embodiment, the method provided herein comprises (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s) ("Cycle 2" and so on); and (ii) administering Compound 1 in cycles of once daily for 21 days followed by 7 days of rest, starting on day 15 of Cycle 1.

Any treatment cycle described herein can be repeated for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In some embodiments, a therapeutically effective amount of Compound 1, Compound 2 or Compound 3, and/or obinutuzumab is administered for 1 to 13 cycles of 28 days (e.g., about 1 year). In some embodiments, a therapeutically effective amount of Compound 1, Compound 2 or Compound 3, and/or obinutuzumab is administered for 1 to 24 cycles of 28 days (e.g., about 2 years). In certain instances, the cycling therapy is not limited to the number of cycles, and the therapy is continued until disease progression. Cycles can in certain instances include varying the duration of administration periods and/or rest periods described herein.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations Used

| | |
|---|---|
| DCM | Dichloromethane |
| DIEA | N,N-Diisopropylethylamine |
| DMF | N,N-Dimethylformamide |
| DMSO | Dimethylsulfoxide |
| ESI | Electrospray ionization |
| EtOAc | Ethyl acetate |
| LCMS | Liquid chromatography mass spectrometry |
| MeOH | Methanol |
| MS | Mass spectrometry |
| NMP | N-Methylpyrrolidone |
| NMR | Nuclear magnetic resonance |
| THF | Tetrahydrofuran |

Example 1: Synthesis of (S)-2-(2,6-Dioxopiperidin-3-yl)-4-((2-fluoro-4-((3-morpholinoazetidin-1-yl)methyl)benzyl)amino)isoindoline-1,3-dione (Compound 1)

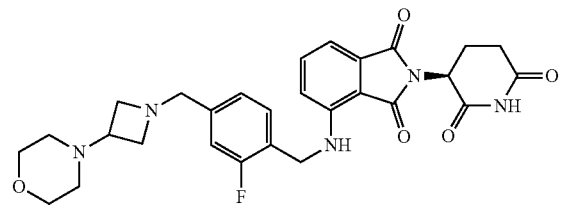 [SMILES: O=C1CC[C@H](N2C(=O)c3cccc(NCc4ccc(CN5CC(N6CCOCC6)C5)cc4F)c3C2=O)C(=O)N1]

(S)-2-(2,6-Dioxopiperidin-3-yl)-4-((2-fluoro-4-(hydroxymethyl)benzyl)amino)isoindoline-1,3-dione: A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1,3-dione as a yellow solid (4.23 g, 56%). LCMS (ESI) m/z 411.8 [M+H]⁺.

(S)-4-((4-(Chloromethyl)-2-fluorobenzyl)amino)-2-(2,6-dioxopiperidin-3-yl)isoindoline-1,3-dione: A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to H₂O (60 mL) cooled to 0° C. with vigorous mixing. The resulting suspension was filtered and the collected solid was washed with H₂O and Et₂O. The solid was dissolved in EtOAc and the solution dried with MgSO₄, filtered and concentrated to provide (S)-4-((4-(chloromethyl)-2-fluorobenzyl)amino)-2-(2,6-dioxopiperidin-3-yl)isoindoline-1,3-dione as a yellow solid (0.600 g, 79%). LCMS (ESI) m/z 430.0 [M+H]⁺.

(S)-2-(2,6-Dioxopiperidin-3-yl)-4-((2-fluoro-4-((3-morpholinoazetidin-1-yl)methyl)benzyl)amino)isoindoline-1,3-dione: To a solution of (S)-4-((4-(chloromethyl)-2-fluorobenzyl)amino)-2-(2,6-dioxopiperidin-3-yl)isoindoline-1,3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee). LCMS (ESI) m/z 536.2 [M+H]⁺.

Example 2: Synthesis of (R)-2-(2,6-Dioxopiperidin-3-yl)-4-((2-fluoro-4-((3-morpholinoazetidin-1-yl)methyl)benzyl)amino)isoindoline-1,3-dione (Compound 2)

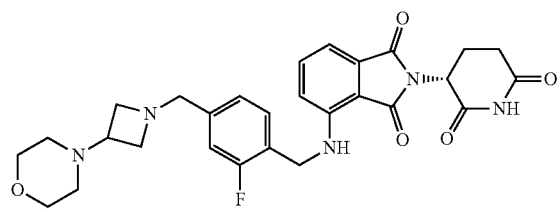 [SMILES: O=C1CC[C@@H](N2C(=O)c3cccc(NCc4ccc(CN5CC(N6CCOCC6)C5)cc4F)c3C2=O)C(=O)N1]

The chiral reverse-phase chromatography described in Example 1 additionally provided (R)-2-(2,6-dioxopiperidin-3-yl)-4-((2-fluoro-4-((3-morpholinoazetidin-1-yl)methyl)benzyl)amino)isoindoline-1,3-dione (16 mg, 97% ee). LCMS (ESI) m/z 535.6 [M+H]⁺.

Example 3: Synthesis of 2-(2,6-Dioxopiperidin-3-yl)-4-((2-fluoro-4-((3-morpholinoazetidin-1-yl)methyl)benzyl)amino)isoindoline-1,3-dione (Compound 3)

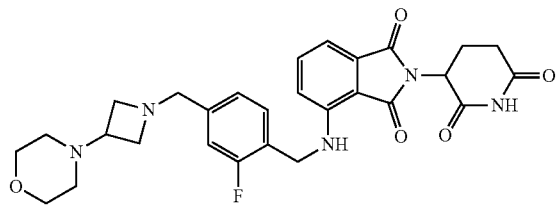 [SMILES: O=C1CCC(N2C(=O)c3cccc(NCc4ccc(CN5CC(N6CCOCC6)C5)cc4F)c3C2=O)C(=O)N1]

(4-Bromo-3-fluoro-phenyl)methanol: A solution of 4-bromo-3-fluoro-benzoic acid (15.0 g, 68.5 mmol) in THF (150 mL) was cooled to 0° C. and borane-dimethyl sulfide complex (13.7 mL, 137 mmol, 10 M in THF) was added dropwise under nitrogen atmosphere. The cooling bath was removed and the mixture was stirred at ambient temperature for 12 hours. The mixture was cooled to 0° C., quenched with MeOH (50 mL) and poured into water (30 mL). The mixture was concentrated under vacuum and the residual aqueous mixture was diluted with ethyl acetate (150 mL) and water (150 mL) and stirred for 15 minutes. The organic phase was removed and the aqueous phase was extracted with ethyl acetate (150 mL×2). The organic fractions were combined, dried with anhydrous sodium sulfate, filtered, and concentrated under vacuum. The residue was purified by silica gel column chromatography (2-10% ethyl acetate in petroleum ether) to give (4-bromo-3-fluoro-phenyl)methanol (13.1 g, 93.3% yield) as a colorless liquid. LCMS (ESI) m/z 187.0 [MH-18⁺]. ¹H NMR (400 MHz, CDCl₃) δ ppm 7.54-7.45 (m, 1H), 7.14 (d, J=9.2 Hz, 1H), 7.00 (d, J=7.9 Hz, 1H), 4.64 (d, J=4.6 Hz, 2H), 2.20 (br s, 1H).

(4-Bromo-3-fluoro-phenyl)methoxy-tert-butyl-dimethyl-silane: A solution of (4-bromo-3-fluoro-phenyl)methanol (13.1 g, 63.9 mmol) and imidazole (12.2 g, 179 mmol) in DMF (150 mL) was cooled to 0° C. and tert-butylchlorodimethylsilane (14.4 g, 95.8 mmol) was added. The cooling bath was removed and the mixture was stirred at ambient temperature for 16 hours. The reaction was poured into chilled water (30 mL), diluted with ethyl acetate (100 mL) and water (100 mL) and stirred for 15 minutes. The organic phase was removed and the aqueous phase was extracted with ethyl acetate (150 mL×2). The organic fractions were combined, washed with saturated NaCl (50 mL×2), dried with anhydrous sodium sulfate, filtered and concentrated under vacuum. The residue was purified by silica gel column chromatography (0-10% ethyl acetate in petroleum ether) to give (4-bromo-3-fluoro-phenyl)methoxy-tert-butyl-dimethyl-silane (18.6 g, 91.2% yield) as a colorless liquid. ¹H NMR (400 MHz, CDCl₃) δ ppm 7.49 (dd, J=7.1, 8.1 Hz, 1H), 7.18-7.08 (m, 1H), 7.01-6.92 (m, 1H), 4.69 (s, 2H), 0.96 (s, 9H), 0.12 (s, 6H).

4-[[tert-Butyl(dimethyl)silyl]oxymethyl]-2-fluoro-benzaldehyde: Under an atmosphere of nitrogen a solution of (4-bromo-3-fluoro-phenyl)methoxy-tert-butyl-dimethyl-silane (18.6 g, 58.3 mmol) in THF (150 mL) was cooled to −78° C. and n-BuLi (25.6 mL, 64.0 mmol, 2.5 M in hexane) was added dropwise. The mixture was stirred at −78° C. for 5 minutes and DMF (5.83 mL, 75.7 mmol) was added. The mixture was stirred at −78° C. for 2 hours and allowed to warm to ambient temperature. The reaction mixture was cooled to 0° C. and quenched with saturated ammonium chloride (60 mL) and water (30 mL). The mixture was extracted with ethyl acetate (2×150 mL) and the combined extracts were dried over sodium sulfate, filtered and concentrated. The residue was purified by silica gel column chromatography (0-2% ethyl acetate in petroleum ether) to give 4-[[tert-butyl(dimethyl)silyl]oxymethyl]-2-fluoro-benzaldehyde (11.5 g, 73.5% yield) as a yellow liquid. MS (ESI) m/z: 269.1 [M+1]$^+$.

3-((4-(((tert-Butyldimethylsilyl)oxy)methyl)-2-fluorobenzyl)amino)phthalic acid: A solution of 4-[[tert-butyl(dimethyl)silyl]oxymethyl]-2-fluoro-benzaldehyde (7.50 g, 27.9 mmol) and 3-aminophthalic acid (5.06 g, 27.9 mmol) in 1:10 acetic acid-MeOH (110 mL) was stirred at 25° C. for 30 minutes and was cooled to 0° C. Borane 2-methylpyridine complex (4.48 g, 41.9 mmol) was added and the mixture was allowed to reach ambient temperature. The mixture was stirred at ambient temperature for 16 hours and the mixture was concentrated under reduced pressure. The residue was diluted with water (25 mL) and ethyl acetate (25 mL) and stirred for 15 minutes. The organic layer was removed and the aqueous layer was extracted with ethyl acetate (30 mL×2). The organic fractions were combined, dried with anhydrous sodium sulfate, filtered, and concentrated. The residue was purified by silica gel column chromatography (2-5% ethyl acetate in petroleum ether) to give 3-((4-(((tert-butyldimethylsilyl)oxy)methyl)-2-fluorobenzyl)amino)phthalic acid (9.90 g, 81.8% yield) as a white solid. LCMS (ESI) m/z: 434.1 [M+1]$^+$.

4-((4-(((tert-Butyldimethylsilyl)oxy)methyl)-2-fluorobenzyl)amino)-2-(2,6-dioxopiperidin-3-yl)isoindoline-1,3-dione: A solution of 3-((4-(((tert-butyldimethylsilyl)oxy)methyl)-2-fluorobenzyl)amino)phthalic acid (11.8 g, 27.2 mmol) and 3-aminopiperidine-2,6-dione hydrochloride (6.72 g, 40.8 mmol) in pyridine (150 mL) was stirred at 120° C. for 12 hours under a nitrogen atmosphere. The mixture was concentrated under reduced pressure and the residue was purified by silica gel column chromatography (2-5% ethyl acetate in petroleum ether) to give 4-((4-(((tert-butyldimethylsilyl)oxy)methyl)-2-fluorobenzyl)amino)-2-(2,6-dioxopiperidin-3-yl)isoindoline-1,3-dione (9.90 g, 69.2% yield) as a yellow solid. LCMS (ESI) m/z: 526.2 [M+1]$^+$.

2-(2,6-Dioxopiperidin-3-yl)-4-((2-fluoro-4-(hydroxymethyl)benzyl)amino)isoindoline-1,3-dione: To a solution of 4-((4-(((tert-butyldimethylsilyl)oxy)methyl)-2-fluorobenzyl)amino)-2-(2,6-dioxopiperidin-3-yl)isoindoline-1,3-dione (9.90 g, 18.8 mmol) in THF (100 mL) was added concentrated sulfuric acid (20.0 mL, 368 mmol) and the mixture was stirred at ambient temperature for 12 hours. The mixture was concentrated under vacuum and the residue was treated with 1:5 ethyl acetate-petroleum ether (20 mL). The resulting suspension was stirred for 30 minutes and filtered. The collected solid was washed with 1:5 ethyl acetate-petroleum ether and dried in vacuum to give 2-(2,6-dioxopiperidin-3-yl)-4-((2-fluoro-4-(hydroxymethyl)benzyl)amino)isoindoline-1,3-dione (6.58 g, 85.2% yield) as a yellow solid. MS (ESI) m/z: 412.0 [M+1]$^+$. $^1$H NMR (400 MHz, DMSO-d$_6$) δ ppm 11.12 (s, 1H), 7.54 (dd, J=7.3, 8.4 Hz, 1H), 7.33 (t, J=7.8 Hz, 1H), 7.16-7.07 (m, 3H), 7.05 (d, J=7.0 Hz, 1H), 6.99 (d, J=8.5 Hz, 1H), 5.33-5.25 (m, 1H), 5.07 (dd, J=5.3, 12.9 Hz, 1H), 4.59 (d, J=6.3 Hz, 2H), 4.47 (d, J=5.8 Hz, 2H), 2.95-2.84 (m, 1H), 2.65-2.52 (m, 2H), 2.09-2.01 (m, 1H).

4-((4-(chloromethyl)-2-fluorobenzyl)amino)-2-(2,6-dioxopiperidin-3-yl)isoindoline-1,3-dione: A solution of 2-(2,6-dioxopiperidin-3-yl)-4-((2-fluoro-4-(hydroxymethyl)benzyl)amino)isoindoline-1,3-dione (6.58 g, 16.0 mmol) in dichloromethane (200 mL) was cooled to 0° C. and thionyl chloride (20.0 mL, 276 mmol) was added dropwise. After complete addition, the cooling bath was removed and the reaction mixture was stirred at ambient temperature for 2 hours. The mixture was concentrated under vacuum and the residue was purified by silica gel column chromatography (1.00-1.25% MeOH in dichloromethane) to give 4-((4-(chloromethyl)-2-fluorobenzyl)amino)-2-(2,6-dioxopiperidin-3-yl)isoindoline-1,3-dione (3.80 g, 55.4% yield) as a yellow solid. LCMS (ESI) m/z: 430.0 [M+1]$^+$. $^1$H NMR (400 MHz, DMSO-d$_6$) δ ppm 11.12 (s, 1H), 7.54 (dd, J=7.3, 8.4 Hz, 1H), 7.38 (t, J=7.9 Hz, 1H), 7.32 (dd, J=1.5, 11.0 Hz, 1H), 7.24 (dd, J=1.6, 7.8 Hz, 1H), 7.16 (t, J=6.3 Hz, 1H), 7.06 (d, J=6.9 Hz, 1H), 6.98 (d, J=8.5 Hz, 1H), 5.08 (dd, J=5.3, 12.9 Hz, 1H), 4.74 (s, 2H), 4.63 (d, J=6.3 Hz, 2H), 2.95-2.85 (m, 1H), 2.66-2.53 (m, 2H), 2.09-2.02 (m, 1H).

2-(2,6-Dioxopiperidin-3-yl)-4-((2-fluoro-4-((3-morpholinoazetidin-1-yl)methyl)benzyl)amino)isoindoline-1,3-dione: To a solution of 4-((4-(chloromethyl)-2-fluorobenzyl)amino)-2-(2,6-dioxopiperidin-3-yl)isoindoline-1,3-dione (215 mg, 0.500 mmol) (prepared as described herein) and 4-(azetidin-3-yl)morpholine hydrochloride (107 mg, 0.600 mmol) in dry DMSO (1.7 mL) was added DIEA (262 µL, 1.50 mmol) and the mixture stirred at ambient temperature for 48 hours. The reaction mixture was diluted with 20% formic acid in DMSO (2.5 mL) and filtered through a membrane syringe filter (0.45 µm nylon). The solution was purified using standard methods to provide 2-(2,6-dioxopiperidin-3-yl)-4-((2-fluoro-4-((3-morpholinoazetidin-1-yl)methyl)benzyl)amino)isoindoline-1,3-dione (173 mg, 64.6% yield). LCMS (ESI) m/z 536.2 [M+H]+.

Example 4: Cell Proliferation and Viability Assay Using CLL Cell Lines

The following are examples of cell-based assays that can be used to determine the anti-proliferative activity and apoptotic effect of compounds described herein using exemplary CLL cell lines (Table 3). The in vitro growth inhibitory activity of Compound 1 described herein was evaluated using a 384-well flow cytometry assay.

TABLE 3

CLL Cell Lines.

| Cell Line | Tumor type | Tumor subtype | Vendor | Culture conditions |
|---|---|---|---|---|
| EHEB | CLL | not specified | DSMZ | RPMI + 10% FBS, |
| WA-C3-CD5+ | CLL | not specified | DSMZ | 1X NEAA, |
| WA-OSEL | CLL | not specified | DSMZ | 2 mM L-glutamine |
| PGA1 | CLL | not specified | DSMZ | |
| HG3 | CLL | not specified | DSMZ | |
| I83-E95 | CLL | not specified | DSMZ | RPMI + 20% FBS, |
| CII | CLL | not specified | DSMZ | 1X NEAA, |
| CI | CLL | not specified | DSMZ | 2 mM L-glutamine |
| Mec2 | CLL | not specified | DSMZ | IMDM +10% FBS |
| Mec1 | CLL | not specified | DSMZ | |

RPMI = RPMI1640;
FBS = fetal bovine serum;
NEAA = non-essential amino acid;
IMDM = Iscove's Modified Dulbecco's medium.

The cell lines were plated under the conditions shown in Table 3 in 384-well flat bottom plates and incubated with increasing concentrations of compound ranging from 0.00015 to 10 µM or dimethyl sulfoxide (DMSO) control. The final concentration of DMSO was 0.1% (v/v). Following the addition of Compound 1 or DMSO and incubation for 120 hours, cell number and cell death were analyzed by flow cytometry (Attune®, Thermo Fisher) using Annexin V and the live-cell impermeant DNA dye, DRAQ7. Phosphatidylserine translocates from the inner layer to the outer layer of the cell membrane early in apoptosis and Annexin V binds to the exposed phosphatidylserine found on the surface of an apoptotic cell. The vital dye DRAQ7 is excluded by intact live cells and only stains cells that have died as a result of apoptosis or necrosis.

Flow cytometry data analysis was then performed using the Flow Jo_v10 software to determine the number of viable cells (Annexin V and DRAQ7 double negative staining cells) and percentage of apoptotic cells (Annexin V positive cells) for each condition. The live cell count for every concentration was normalized to the DMSO control (considered as 100% viable cells) to calculate the percentage of viable cells remaining after treatment and graphed using GraphPad Prism 7.03. The $IC_{50}$ (50% inhibitory concentration) and $E_{max}$ (maximum efficacy achieved) values were then calculated by performing nonlinear regression curve fitting using log (inhibitor) vs. normalized response—variable slope analysis on GraphPad Prism 7.03. Area under the curve (AUC) was calculated by performing area under curve analysis on GraphPad Prism 7.03. Similarly, for apoptosis analysis, the percentage of apoptosis combining both "early" (Annexin V positive and DRAQ7 negative) and "late" apoptosis (Annexin V and DRAQ7 positive) cell gates relative to DMSO was graphed using GraphPad Prism 7.03. The AUC, $EC_{50}$ (concentration of Compound 1 that produces half-maximal apoptosis response) and $Y_{max}$ (maximal percentage of apoptosis achieved) values from apoptosis curves were calculated by performing area under curve analysis and nonlinear regression curve fitting using log (agonist) vs. normalized response—Variable slope analysis on GraphPad Prism 7.03.

As shown in Table 4, Compound 1 dose-response proliferation curves for the panel of CLL cell lines and non-linear curve-fit regression were used to determine $IC_{50}$, AUC, and $E_{max}$ for % viable cells ($E_{max}$ for viability varies between 100 at low doses and 0 at high doses, which corresponds to inhibition of all viable cells), and Compound 1 dose-response apoptosis curves were used to determine the $EC_{50}$, AUC, and $Y_{max}$ for % apoptosis ($Y_{max}$ for apoptosis varies from 0 at low doses and 100 at higher doses which corresponds to death of all cells).

Compound 1 was found to have antiproliferative activity and/or apoptotic effects in CLL cell lines (Table 4).

TABLE 4

Antiproliferative Activity and Apoptotic Effect of Compound 1 in CLL Cell Lines.

| Cell Line | % Viable Cells | | | Apoptosis | | |
|---|---|---|---|---|---|---|
| | AUC | $IC_{50}$ | $E_{max}$ | AUC | $EC_{50}$ | $Y_{max}$ |
| EHEB | 319.3 | 0.0303 | 28.68 | 65.03 | 0.5062 | 8.42 |
| WA-C3-CD5+ | 474.8 | 0.53 | 44.2 | 162.9 | 0.05244 | 17.47 |
| WA-OSEL | 616.1 | 10 | 54.42 | 69.39 | 0.112 | 7.38 |
| PGA1 | 736.7 | 10 | 69.21 | 48.94 | 0.1219 | 5.075 |
| HG3 | 676.2 | 10 | 59.58 | 131.5 | 0.1107 | 14.28 |
| I83-E95 | 259.2 | 0.01728 | 21.6 | 358.4 | 0.06111 | 40.69 |
| CII | 926.1 | 10 | 78.23 | 238.1 | 0.145 | 26.11 |
| CI | 603.9 | 9.701 | 53.58 | 123.2 | 0.02294 | 13.01 |

TABLE 4-continued

Antiproliferative Activity and Apoptotic Effect of Compound 1 in CLL Cell Lines.

| Cell Line | % Viable Cells | | | Apoptosis | | |
|---|---|---|---|---|---|---|
| | AUC | $IC_{50}$ | $E_{max}$ | AUC | $EC_{50}$ | $Y_{max}$ |
| Mec2 | 312.5 | 0.07552 | 25.55 | 339.8 | 0.01331 | 35.28 |
| Mec1 | 866.5 | 10 | | 83.45 | 302.4 | 0.2097 | 36.61 |

AUC = area under the curve;
$IC_{50}$ = 50% inhibitory concentration (μM);
$E_{max}$ = maximum efficacy eliminating tumor cells achieved expressed as the percentage of tumor cells remaining;
$EC_{50}$ = compound concentration that produces half-maximal apoptosis response (μM);
$Y_{max}$ = calculated percent of control at highest concentration of Compound 1.

Example 5: Cell Proliferation and Viability Assay for B-Cell CLL Patient Cells

The following are examples of cell-based assays that can be used to determine the anti-proliferative activity and apoptosis effect of compounds described herein using exemplary CLL patient cells. The effect of Compound 1 on the viability and apoptosis of CLL B cells was assessed utilizing an ex vivo model.

CLL is characterized by accumulation of clonal $CD5^+$ $CD19^+$ lymphocytes resistant to apoptosis. The effect of Compound 1 on the viability and apoptosis of CLL B cells was assessed utilizing an ex vivo model where primary CLL cells from patient-derived blood were stimulated with 10% fetal bovine serum (FBS), 5 ng/mL recombinant human interleukin-4 (rh IL-4), 10 ng/mL recombinant human interleukin-10 (rh IL-10) and co-cultured with fibroblast expressing surface CD154 (CD40L). The percentage of cells staining with Annexin V and/or DRAQ-7 was measured by flow cytometry assay after 3, 6 or 10 days of incubation with vehicle control or with increasing concentrations of Compound 1 ranging from 0.001 to 1 μM. Peripheral blood mononuclear cells (PBMCs) from CLL patients (Table 5) containing 70%-95% of $CD5^+CD19^+$ tumor cells were cultured on a monolayer of CD154-expressing fibroblasts in 24-well plates at a density of patient cells of $0.8 \times 10^6$ cells/well in RPMI 1640 medium supplemented with 10% FBS, 5 ng/mL rh IL-4 and 10 ng/mL rh IL-10 and were treated with vehicle control (0.1% DMSO) or increasing concentrations of Compound 1 ranging from 0.001 to 1 μM. After treatment, flow cytometric analysis was used to determine the number of cells that were viable or apoptotic.

TABLE 5

Characteristics of the CLL Samples Used.

| CLL Pt | Tumor Burden | IGHV Mutation Status | Cytogenetics | Prior Therapy |
|---|---|---|---|---|
| 1 | 89% | Mutated | del(13q); tri12 | N |
| 2 | 94% | Non-Mutated | del(13q) | N |
| 3 | 94% | Non-Mutated | del(13q) | N |
| 4 | 78% | Mutated | del(13q) | N |
| 5 | 80% | Mutated | del(13q) | N |
| 6 | 95% | Non-Mutated | del(13q) + t(6;17) | N |
| 7 | 62% | Non-Mutated | tri12; del(11q22.3) | N |
| 8 | 91% | Mutated | del(13q) | N |

TABLE 5-continued

Characteristics of the CLL Samples Used.

| CLL Pt | Tumor Burden | IGHV Mutation Status | Cytogenetics | Prior Therapy |
|---|---|---|---|---|
| 9 | 83% | Mutated | tri12; del(13q) | N |
| 10 | 72% | nd | Richter's Syndrome | N |

IGHV status refers to somatic mutation in IGHV gene of CLL cells as compared with the gene sequence of germ-line.
Nd = not done/unknown;
tri = trisomy;
del = deletion;
t = translocation.

After 3, 6 or 10 days of compound treatment, cells were incubated with Annexin V to capture the externalization of phosphatidylserine as a result of disturbed lipid asymmetry in the plasma membrane of cells, a well-characterized event in apoptosis, and the vital far-red fluorescent DNA dye DRAQ-7, that only stains the nuclei of dead and permeabilized cells, and analyzed by flow cytometry (Attune®, Thermo Fisher). Analysis was then performed to determine the percentage of viable live cells (Annexin V and DRAQ-7 double negative staining cells) using FlowJo_V10 and graphed with GraphPad Prism 7.03 software. The live cell count for every condition was normalized to the DMSO control (considered as 100% viable cells) to calculate the percentage of viable cells remaining after treatment. The $IC_{50}$ (50% inhibitory concentration) and $E_{max}$ (maximum efficacy eliminating tumor cells achieved) values were then calculated by performing nonlinear regression curve fitting using log(inhibitor) vs. normalized response—variable slope analysis on GraphPad Prism 7.03. Area under the curve (AUC) value of the viable cell counts over time was calculated by performing area under curve analysis on GraphPad Prism 7.03 (Table 6).

A potent dose-dependent inhibition of CLL-cell proliferation was observed for compound 1 in all CLL patient samples evaluated (Table 6), with compound 1 concentrations that led to 50% inhibition of growth ($IC_{50}$) between 0.0001 and 0.003 µM. The sensitivity to compound 1 was independent of IGHV mutation status and other chromosomal characteristics.

TABLE 6

Antiproliferative Effect of Compound 1 on Ex Vivo Cultures of CLL Patient Cells.

| Patient number | $IC_{50}$ | $E_{max}$ | AUC |
|---|---|---|---|
| Pt1 | 1.63E−08 | 4.621 | 32.79 |
| Pt2 | 0.001048 | 30.58 | 181.6 |
| Pt3 | 0.000723 | 12.98 | 106.1 |
| Pt4 | 1.63E−08 | 6.501 | 44.01 |
| Pt5 | 0.000305 | 22.77 | 139.6 |
| Pt6 | 0.002748 | 27.42 | 154.9 |
| Pt7 | 3.6E−05 | 5.873 | 44.86 |
| Pt8 | 0.000209 | 4.82 | 75.03 |
| Pt9 | 6.52E−05 | 4.141 | 48.14 |
| Pt10 | 0.000129 | 10.21 | 57.87 |

AUC = area under the curve;
$IC_{50}$ = 50% inhibitory concentration (µM);
$E_{max}$ = % maximum efficacy eliminating tumor cells achieved expressed as the percentage of tumor cells remaining;
Pt = patients

Example 6: Antiproliferative Effect of Compound 1 in Combination with Obinutuzumab in B-Cell CLL Patient Cells Obinutuzumab (GA101) is a humanized, glycoengineered type 2 antibody targeted against CD20. Obinutuzumab showed superior efficacy, as compared to rituximab, by inducing direct cell death and enhanced antibody-dependent cellular cytotoxicity. The effect of treatment with Compound 1 in combination with obinutuzumab on the proliferation and survival of CLL B cells was assessed utilizing an ex vivo model where primary CLL cells from patient-derived blood were stimulated to proliferate with 10% fetal bovine serum (FBS), 5 ng/mL recombinant human interleukine-4 (rh IL-4), 10 ng/mL recombinant human interleukine-10 (rh IL-10) and co-cultured with fibroblast expressing surface CD154 (CD40L) in a 96 well plate format.

Peripheral blood mononuclear cells (PBMCs) from CLL patients (Table 7) containing 52%-86% of $CD5^+CD19^+$ tumor cells were cultured at a density of $0.06$-$0.1 \times 10^6$ cells/well on a monolayer of CD154-expressing fibroblasts at a density of $0.09 \times 10^6$ cells/well in 96-well plates in RPMI 1640 medium supplemented with 10% FBS, 5 ng/mL rh IL-4 and 10 ng/mL rh IL-10. The cells were treated with vehicle control (0.1% DMSO) or increasing concentrations of Compound 1 ranging from 0.0001 to 1 µM and GA101 at concentrations ranging from 8 ng/mL to 5 ug/mL across all the different concentrations of Compound 1. After 144 h of treatment with both the agents, flow cytometric analysis was used to determine the number of tumor cells that were viable or apoptotic.

The tumor cell count was assessed by staining the patient PBMCs in each condition with tumor cell surface markers CD5 & CD19 along with Live/Dead fixable dye to exclude the dead cells and followed by intracellular staining for Caspase3 antibody to identify the apoptotic cells and was measured by flow cytometry (Attune NxT, Thermo Fisher). The live tumor cell count for each condition was calculated by normalizing to the precision count beads added to each sample.

TABLE 7

Characteristics of the CLL Samples Used.

| CLL Pt | Tumor Burden | IGHV Mutation Status | Cytogenetics | Prior Therapy |
|---|---|---|---|---|
| 11 | 85% | Non-Mutated | del(13q) | N |
| 12 | 75% | Non-Mutated | del(13q) (35%) | N |
| 13 | 30% | Mutated | del(13q); tri12 | N |
| 14 | 86% | Mutated | del(13q); anamoly in cell interphase (86%) | Mitomycin |

The live tumor cell count was then normalized to the DMSO control (considered as 100% viable) to calculate the percentage of viable cells remaining after treatment. The normalized percentage of tumor cells was then represented as a heat map using Graph Pad Prism 8.0.0 to indicate the degree of tumor toxicity for each of the combinations (FIG. 1). Based on the data shown in FIG. 1, synergy/additivity calculations were performed using the HSA and Bliss Independence Model. Either synergistic or additive effect was observed in three (pt11, 12 & 13) out of four patient samples tested.

For apoptosis analysis, the percentage of apoptosis combining both "early" (Caspase 3 positive and Live-Dead fixable dye negative) and "late" apoptosis (Caspase 3 and Live-Dead fixable dye positive) cell gates subtracting the baseline DMSO value was graphed using GraphPad Prism 8.0.0.0. The $Y_{max}$ (maximal percentage of apoptosis achieved) values from apoptosis curves were calculated by performing a nonlinear regression curve fitting using log (agonist) vs. normalized response—Variable slope analysis and identifying the maximum value on GraphPad Prism 8.0.0 (Table 8). Obinutuzumab induced apoptosis alone and enhanced moderately compound 1 ability to induce apoptosis.

TABLE 8

Maximum Apoptosis Effect of Compound 1 in combination with Obinutuzumab.

| Concentrations of Obinutuzumab | Ymax of Pt 11 (%) | Ymax of Pt 12 (%) | Ymax of Pt 13 (%) | Ymax of Pt 14 (%) |
|---|---|---|---|---|
| DMSO + Cpd1 DRC | 18.81 | 19.11 | 29.40 | 24.11 |
| 8 ng/mL + Cpd1 DRC | 16.73 | 17.82 | 36.37 | 17.58 |
| 40 ng/mL + Cpd1 DRC | 24.43 | 20.94 | 38.57 | 17.00 |
| 200 ng/mL + Cpd1 DRC | 32.17 | 21.44 | 38.25 | 19.14 |
| 1 µg/mL + Cpd1 DRC | 30.93 | 24.91 | 38.96 | 25.82 |
| 5 µg/mL + Cpd1 DRC | 29.96 | 23.65 | 41.95 | 25.23 |
| Obinutuzumab alone | 27.98 | 24.91 | 35.87 | 25.82 |

Example 7: Phase I Clinical Study

A phase 1b, multi-center, open-label study is conducted to determine the safety, pharmacokinetics, and preliminary efficacy of Compound 1 in combination with obinutuzumab in subjects with relapsed or refractory chronic lymphocytic leukemia/small lymphocytic lymphoma (R/R CLL/SLL).

Objectives: Primary objectives of the study are to determine the safety and tolerability of Compound 1 in combination with obinutuzumab in subjects with R/R CLL/SLL. Another primary objective is to define the maximum tolerated dose (MTD) and/or the recommended Phase 2 dose (RP2D) of Compound 1 in combination with obinutuzumab in subjects with R/R CLL/SLL.

The secondary objectives are to evaluate the preliminary efficacy of Compound 1 in combination with obinutuzumab in subjects with R/R CLL/SLL and to determine the pharmacokinetics (PK) of Compound 1 when used in combination with obinutuzumab in subjects with R/R CLL/SLL.

Study Design: This is an open-label, phase 1b study to assess the safety, PK and preliminary efficacy of Compound 1 administered orally in combination with obinutuzumab in subjects with R/R CLL/SLL. All eligible subjects must be relapsed or refractory to at least 2 prior lines of CLL/SLL therapy, including a Bruton's tyrosine kinase (BTK) inhibitor. All subjects must have an indication for treatment at study entry. The study is conducted in two parts: Part A (dose escalation) and Part B (dose expansion). The dose escalation (Part A) evaluates the safety, tolerability and PK of escalating doses of Compound 1 given in combination with intravenous obinutuzumab to determine the MTD and RP2D of Compound 1 when given in combination with obinutuzumab. Compound 1 is administered orally once daily (QD) on planned dosing days. If the starting dose/schedule is not tolerated, a lower dose or less intense schedule may be explored. All treatments is administered until disease progression, unacceptable toxicity, death, or subject/physician decision to withdraw, for up to 24 cycles of total treatment.

Following completion of dose escalation (Part A), a selected expansion cohort (Part B) of approximately 20 evaluable subjects receives Compound 1 in combination with obinutuzumab.

The total daily dose to be administered to the next dose cohort is determined based on the calculation, in consideration of available safety, PK and PD data collected.

In Part B, dose expansion may occur at the MTD established in the dose escalation phase, or at an alternative tolerable dosing schedule, based on review of safety, PK, and PD data from Part A.

Best overall response is determined by criteria set forth in the iwCLL (Table 1). Response is assessed by the Investigator. One or more dosing regimens may be selected for cohort expansion.

Study Population: Study subjects will include men and women, 18 years or older, with R/R CLL/SLL who have failed prior therapy as detailed in the inclusion/exclusion criteria.

Inclusion Criteria: Subjects must satisfy the following criteria to be enrolled in the study:

1. Subject is ≥18 years of age the time of signing the informed consent form (ICF).

2. Subject must understand and voluntarily sign an ICF prior to any study-related assessments/procedures being conducted.

3. Subject is willing and able to adhere to the study visit schedule and other protocol requirements.

4. Subject must have a documented diagnosis of CLL/SLL requiring treatment (iwCLL Guidelines for the Diagnosis and Treatment of CLL (Tables 1 and 2). In addition:

a. Presence of clinically measurable disease determined by at least one of the factors listed:
  nodal lesion that measures ≥1.5 cm in longest dimension (LD) and ≥1.0 cm in longest perpendicular dimension (LPD), or
  spleen that measures ≥14 cm in longest vertical dimension (LVD) with a minimum of 2 cm enlargement, or
  liver that measures ≥20 cm in LVD with a minimum of 2 cm enlargement, or
  peripheral blood B lymphocyte count >5000/µL 5. Subject must meet the criteria for relapsed and/or refractory disease according to the iwCLL guidelines to at least two prior lines of therapy.

6. All eligible subjects must be relapsed after or be refractory to at least two prior lines of therapy one of which must have included an approved BTK inhibitor.

7. Subject has an Eastern Cooperative Oncology Group (ECOG) performance status of 0-2 (Table 2).

8. Subjects who meet the following laboratory parameters:
a. Absolute neutrophil count (ANC) ≥1,500 cells/mm$^3$ or ≥1000 cells/mm$^3$ if secondary to bone marrow involvement by disease.
b. Platelet count ≥100,000 cells/mm$^3$ (100×10$^9$/L) or ≥50,000 cells/mm$^3$ (50×10$^9$/L) if secondary to bone marrow involvement by disease.
c. Serum aspartate transaminase (AST/SGOT) or alanine transaminase (ALT/SGPT)<3.0×upper limit of normal (ULN).
d. Serum bilirubin <1.5×ULN unless due to Gilbert's syndrome.
e. Calculated creatinine clearance of ≥60 mL/min.

9. Agree to scheduled pregnancy testing and Pregnancy Risk Management Plan during the course of the study, and after the end of study treatment. This applies even if the subject practices true abstinence from heterosexual contact. A female of childbearing potential (FCBP) is a female who: 1) has achieved menarche at some point, 2) has not undergone a hysterectomy or bilateral oophorectomy, or 3) has not been naturally postmenopausal (amenorrhea following cancer therapy does not rule out childbearing potential) for at least 24 consecutive months (i.e., has had menses at any time in the preceding 24 consecutive months) and must:

a. Have two negative pregnancy tests as verified by the Investigator prior to starting study therapy. She must agree to ongoing pregnancy testing during the course of the study, and after end of study therapy. This applies even if the subject practices true abstinence from heterosexual contact.

b. Either commit to true abstinence from heterosexual contact (which must be reviewed on a monthly basis and source documented) or agree to use, and be able to comply with, two reliable forms of contraception without interruption as defined in the PPP and provided to the subject at the time of informed consent, 28 days prior to starting Compound 1, during the study therapy (including during dose interruptions), and for 28 days after discontinuation of study therapy or 18 months after last dose of obinutuzumab, whichever is the last.

Male subjects must practice true abstinence (which must be reviewed on a monthly basis) or agree to use a condom during sexual contact with a pregnant female or a female of childbearing potential while participating in the study, during dose interruptions and for at least 3 months following investigational product discontinuation, or longer if required for each compound and/or by local regulations, even if he has undergone a successful vasectomy. (True abstinence is acceptable when this is in line with the preferred and usual lifestyle of the subject. Periodic abstinence (e.g., calendar, ovulation, symptothermal, post-ovulation methods) and withdrawal are not acceptable methods of contraception.)

Exclusion Criteria: The presence of any of the following will exclude a subject from enrollment:

1. Subject has any significant medical condition, laboratory abnormality, or psychiatric illness that would prevent the subject from participating in the study.
2. Subject has any condition including the presence of laboratory abnormalities which places the subject at unacceptable risk if he/she were to participate in the study.
3. Subject has any condition that confounds the ability to interpret data from the study. 4. Prior allogeneic stem cell transplant (SCT)/bone marrow transplant within 12 months of signing the ICF. Subjects who received allogeneic SCT≥12 months before signing the ICF may be eligible provided there is no ongoing graft-versus-host disease (GVHD) and no ongoing immune suppression therapy.
5. Ongoing or active infection requiring parenteral antibiotics.
6. Uncontrolled intercurrent illness including, but not limited to:

a. Uncontrolled diabetes mellitus. The glycemic targets for subjects with diabetes should take into consideration age, comorbidities, life expectancy, and functional status of the subjects and follow established guidelines (e.g., International Diabetes Federation, the European Diabetes Working Party guidelines, and the American Diabetes Association). For younger (<70 years old) or subjects with life expectancy ≥10 years, the target glycosylated hemoglobin, type A1C (HbA1c) should be <7.0%. The target HbA1c for older (≥70 years old) subjects or subjects with life expectancy <10 years should be <8.0%. Consultation with an endocrinologist is recommended when deciding if diabetes is optimally controlled. Subjects with a stable HbA1c greater than the suggested target may be enrolled upon discussion with the medical monitor.

b. Chronic symptomatic congestive heart failure (Class III or IV of the New York Heart Association Classification for Heart Disease).

c. Active central nervous system involvement as documented by spinal fluid cytology or imaging.

d. Uncontrolled autoimmune hemolytic anemia or thrombocytopenia.

e. Other concurrent severe and/or uncontrolled concomitant medical conditions that could cause unacceptable safety risks or compromise compliance with protocol.

7. Subject has received prior systemic anti-cancer treatment (approved or investigational) ≤5 half-lives or 4 weeks prior to starting Compound 1, whichever is shorter.
8. Subject has received prior CAR-T or other T-cell targeting treatment (approved or investigational)≤4 weeks prior to starting Compound 1.
9. Subject has received prior therapy with CRBN-modulating drug (e.g., lenalidomide, avadomide/CC-122, pomalidomide)≤4 weeks prior to starting Compound 1.
10. History of second malignancies with life expectancy of ≤2 years or requirement of therapy that would confound study results. This does not include the following:

a. Basal cell carcinoma of the skin.
b. Squamous cell carcinoma of the skin.
c. Carcinoma in situ of the cervix.
d. Carcinoma in situ of the breast.
e. Carcinoma in situ of the bladder.
f. Incidental histologic finding of prostate cancer (Tumor, Node, Metastasis [TNM] TNM stage of T1a or T1b).

11. Known seropositivity for or history of active viral infection with human immunodeficiency virus (HIV), or hepatitis B or C virus (HBV, HCV). Hepatitis B screening is mandatory for all patients (HBsAg and anti-HBc). Patients with active hepatitis B disease should not be treated with obinutuzumab. Patients should be referred to a specialist if they are carriers before treatment starts (see PI or SmPC). Subjects who are positive for anti-HBc and/or anti-HBs but negative for HBsAg and HBV DNA may be treated after consultation with a hepatologist.
12. Peripheral neuropathy ≥Grade 2.
13. Use of systemic corticosteroids in doses greater than prednisone equivalent to 20 mg/day.
14. Medicines with high probability to cause QT prolongation or torsades de pointes. Subjects on chronic medications in this category may enroll after discussion with the medical monitor if changing these medications are not in the best medical interest of the patient.
15. History of hypersensitivity to Immunomodulatory Imide Drugs (IMiDs®) (lenalidomide, pomalidomide, thalidomide).
16. Impaired cardiac function or clinically significant cardiac diseases, including any of the following:

a. LVEF<45% as determined by MUGA scan or ECHO.
b. Complete left bundle branch, or bifascicular, block.
c. Congenital long QT syndrome.
d. Persistent or uncontrolled ventricular arrhythmias or atrial fibrillation.
e. QTcF>470 msec on Screening ECG (mean of triplicate recordings).
f. Unstable angina pectoris or myocardial infarction ≤6 months prior to starting Compound 1.
g. Uncontrolled congestive heart failure or uncontrolled hypertension.

17. Persistent diarrhea or malabsorption ≥NCI CTCAE Grade 2, despite medical management.
18. Active disease transformation (i.e., Richter's Syndrome); subjects with Richter's Syndrome that has resolved >2 years from signing the ICF are eligible.
19. Known acute or chronic pancreatitis.
20. Pregnant or lactating females.

21. Hypersensitivity to obinutuzumab or to any of the excipients.

Length of Study: The entire study is expected to last approximately 4 years. The study consists of three phases: Screening, Treatment and Follow-up. During the Screening Phase, lasting up to 28 days from the time of signing informed consent to first dose administered, subjects undergo assessments to determine their eligibility.

Subjects who qualify for enrollment into the study will enter the Treatment Phase, during which subjects receive investigational product(s) [IP(s)] at a predetermined dose and schedule until the underlying CLL/SLL has progressed or the subject has discontinued IP treatment for unacceptable toxicity or other reasons.

The Follow-up Phase begins at study treatment discontinuation. Subjects have a visit at the end of treatment as soon as possible once IP has been discontinued and at 28 days after the last dose of IP. All subjects discontinued for any reason other than progressive disease, withdrawal of consent, or death, is contacted every 90 days following the date of the 28-day follow-up visit for information regarding the status of their disease and for the type and start date for any subsequent anticancer therapy. Efficacy assessments (including clinical, laboratory tests, and CT scans) continue until documented PD or initiation of subsequent anti-CLL therapy.

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Study Treatments: Subjects begin treatment upon confirmation of eligibility.

Obinutuzumab is administered as an intravenous infusion. Obinutuzumab is administered on Cycle 1 Days 1, 2, 8, and 15. Obinutuzumab is administered at a dose of 100 mg on Cycle 1 Day 1 and 900 mg on Cycle 1 Day 2 and 1000 mg on each of Cycle 1 Day 8 and Cycle 1 Day 15. The dose of obinutuzumab on Days 1 and 2 of Cycle 1 may be adjusted per institutional practice as long as the combined dose equals 1000 mg. Obinutuzumab is administered at a dose of 1000 mg on Day 1 of Cycles 2 through 6.

All active subjects who are receiving clinical benefit in the opinion of the treating investigator may continue to receive study treatment up to a maximum of 24 cycles of Compound 1, or until disease progression (PD), unacceptable toxicity, or discontinuation for any other reason, whichever is earlier. In the event Compound 1 is discontinued prior to obinutuzumab, obinutuzumab will also be discontinued. In the event that obinutuzumab is permanently discontinued, Compound 1 may continue. Subjects who achieve minimal residual disease (MRD) negativity (in both peripheral blood and bone marrow) lasting for a minimum of 3 months in duration have the option to discontinue study treatment; study treatment in these subjects may be resumed at the time of MRD positivity.

Overview of Key Efficacy Assessments: Efficacy assessments include 1) overall response rate (ORR) [complete response (CR), complete response with incomplete marrow recovery (CRi), nodular partial response (nPR), partial response (PR), partial response with lymphocytosis (PRL)] as assessed by the iwCLL 2018 guidelines (Tables 1 and 2); 2) clinical laboratory evaluations; 3) tumor imaging assessment (CT scan), 4) one marrow aspirate/biopsy; 5) ECOG Performance status; 6) B-Symptom evaluation.

Overview of Key Safety Assessments: Safety assessments include 1) adverse events using the NCI CTCAE v 5 unless otherwise specified for selected AEs; 2) vital signs; 3) physical examination; 4) concomitant medications and procedures; 5) electrocardiogram (ECG); 6) clinical laboratory assessments (including hematology and clinical chemistry with renal and liver function assessment); 7) pregnancy testing; 8) left ventricular ejection fraction (LVEF).

Overview of Pharmacokinetic assessments: Blood samples are collected according to intensive and sparse sampling strategies to characterize Compound 1 PK when administered in combination with obinutuzumab. Obinutuzumab serum concentrations are measured at specified timepoints. Trends in exposure-response relationships of Compound 1 and markers of efficacy, safety, and biological response is also explored.

Example 8: Phase I Clinical Study

A phase 1b, multi-center, open-label study is conducted to determine the safety, pharmacokinetics, and preliminary efficacy of Compound 1 in combination with obinutuzumab in subjects with relapsed or refractory chronic lymphocytic leukemia/small lymphocytic lymphoma (R/R CLL/SLL).

Objectives: Primary objectives of the study are to determine the safety and tolerability of Compound 1 in combination with obinutuzumab in subjects with R/R CLL/SLL. Another primary objective is to define the maximum tolerated dose (MTD) and/or the recommended Phase 2 dose (RP2D) of Compound 1 in combination with obinutuzumab in subjects with R/R CLL/SLL.

The secondary objectives are to evaluate the preliminary efficacy of Compound 1 in combination with obinutuzumab in subjects with R/R CLL/SLL and to determine the pharmacokinetics (PK) of Compound 1 when used in combination with obinutuzumab in subjects with R/R CLL/SLL.

Study Design: This is an open-label, phase 1b study to assess the safety, PK and preliminary efficacy of Compound 1 administered orally in combination with obinutuzumab in subjects with R/R CLL/SLL. All eligible subjects must be relapsed or refractory to at least 2 prior lines of CLL/SLL therapy, including an inhibitor of B-cell receptor signaling (approved Bruton's tyrosine kinase [BTK] inhibitor [BTKi] or phosphoinositide 3-kinase inhibitor [PI3Ki]) or venetoclax. Prior therapy with regimen containing obinutuzumab is permitted.

All subjects must have an indication for treatment at study entry. The study is conducted in two parts: Part A (dose escalation) and Part B (dose expansion). The dose escalation (Part A) evaluates the safety, tolerability and PK of escalating doses of Compound 1 given in combination with intravenous obinutuzumab to determine the MTD and RP2D of Compound 1 when given in combination with obinutuzumab. Approximately 25-30 subject can be enrolled in Part A. The actual number depends on the number of schedules/dose levels required to determine the MTD or RP2D. Compound 1 is administered orally once daily (QD) on planned dosing days. The starting dose/schedule of Compound 1 is 0.2 mg/day for 7 consecutive days (initiated on Cycle 1 Day 15) followed by 7 days off study drug every 14 days (7/14-day schedule) in each 28-day cycle. If the starting dose/schedule is not tolerated, a lower dose or less intense schedule may be explored. All treatments is administered until disease progression, unacceptable toxicity, death, or subject/physician decision to withdraw, for up to 24 cycles or 2 years of total treatment.

Following completion of dose escalation (Part A), a selected expansion cohort (Part B) of approximately 20 evaluable subjects receives Compound 1 in combination with obinutuzumab. An evaluation of the safety/tolerability, PK and preliminary efficacy of additional Compound 1 combination expansion cohorts with other CLL/SLL agents of interest (e.g., rituximab; ibrutinib; venetoclax; or other agent) may be initiated in parallel in Part B. Enrollment occurs globally, including in the United States (US), Europe, and/or Canada for the study. Additional countries and sites may be added for Part B and/or Part A.

A Bayesian Logistic Regression Model (BLRM) (Neuenschwander B, et al. *Statistics in medicine* 2008, 27:2420-39) with overdose control (EWOC) (Babb J, et al. *Statistics in medicine* 1998, 17:1103-20) is utilized to help guide Compound 1 dose escalation/de-escalation decisions.

A subject evaluable for dose limiting toxicity (DLT) is defined as one that: 1) has received at least 75% of planned Compound 1 and obinutuzumab dose during Cycle 1 Day 15 to Cycle 2 Day 14 without experiencing a DLT, or 2) experienced a DLT after receiving at least 1 dose or fraction thereof of Compound 1 during Cycle 1 Day 15 to Cycle 2 Day 14.

Alternate Compound 1 dosing schedule (e.g., 5/14 days, 14/28 days, or 21/28 days) may be explored based on review of available clinical safety, PK and PD data. If a new schedule is explored the total planned dose intensity for the cycle will not exceed that of a previously tolerated schedule, or a currently allowed escalation thereof, and the maximum daily dose will not exceed a 100% increase of a previously tolerated daily dose on any schedule. The BLRM will be adjusted with each schedule as covariates while a different schedule may be explored.

The first cohort is treated under a 7/14 day dosing schedule at a daily dose of 0.2 mg. If toxicity is observed at the starting dose, a dose level-1 (DL-1) of 0.1 mg/day may be explored.

The total daily dose to be administered to the next dose cohort is determined based on the calculation or the dose recommended by BLRM (Neuenschwander B, et al. *Statistics in medicine* 2008, 27:2420-39) with overdose control (EWOC) (Babb J, et al. *Statistics in medicine* 1998, 17:1103-20) method, in consideration of available safety, PK and PD data collected. Planned dose levels are 0.1 mg, 0.2 mg, 0.4 mg, 0.6 mg, 0.8 mg, 1.2 mg and 1.6 mg. It is however possible that the actual dose levels selected for the trail may be different from the provisional dose levels, based on the review of safety, PK, PD and efficacy data.

The target toxicity (DLT) rate for the Compound 1 MTD in combination with obinutuzumab is 25%; the minimal sample size per dose cohort will be 3 subjects. The total number of subjects required for determination of Compound 1 MTD in combination with obinutuzumab is estimated at approximately 25-30 subjects.

In Part B, dose expansion may occur at the MTD established in the dose escalation phase, or at an alternative tolerable dosing schedule, based on review of safety, PK, and PD data from Part A.

Best overall response is determined by criteria set forth in the International Workshop on Chronic Lymphocytic Leukemia (iwCLL) (Table 1). Response is assessed by the Investigator. One or more dosing regimens may be selected for cohort expansion.

Study Population: Study subjects will include men and women, 18 years or older, with R/R CLL/SLL who have failed prior therapy as detailed in the inclusion/exclusion criteria.

Inclusion Criteria: Subjects must satisfy the following criteria to be enrolled in the study:
1. Subject is ≥18 years of age the time of signing the informed consent form (ICF).
2. Subject must understand and voluntarily sign an ICF prior to any study-related assessments/procedures being conducted.
3. Subject is willing and able to adhere to the study visit schedule and other protocol requirements.
4. Subject must have a documented diagnosis of CLL/SLL requiring treatment (iwCLL Guidelines for the Diagnosis and Treatment of CLL (Tables 1 and 2). In addition:
   a. Presence of clinically measurable disease determined by at least one of the factors listed:
      nodal lesion that measures ≥1.5 cm in longest dimension (LD) and ≥1.0 cm in longest perpendicular dimension (LPD), or
      spleen that measures ≥14 cm in longest vertical dimension (LVD) with a minimum of 2 cm enlargement, or
      liver that measures ≥20 cm in LVD with a minimum of 2 cm enlargement, or
      peripheral blood B lymphocyte count >5000/µL
5. Subject must meet the criteria for relapsed and/or refractory disease according to the iwCLL guidelines to at least two prior lines of therapy.
6. All eligible subjects must be relapsed after or be refractory to at least two prior lines of therapy one of which must have included an inhibitor of B-cell receptor signaling (approved BTKi or PI3Ki) or venetoclax. Prior therapy with regimen containing obinutuzumab is permitted.
7. Subject has an Eastern Cooperative Oncology Group (ECOG) performance status of 0-2 (Table 2).
8. Subjects who meet the following laboratory parameters:
   a. Absolute neutrophil count (ANC)≥1,500 cells/mm$^3$ or ≥1000 cells/mm$^3$ if secondary to bone marrow involvement by disease.
   b. Platelet count≥100,000 cells/mm3 ($100\times10^9$/L) or ≥50,000 cells/mm$^3$ ($50\times10^9$/L) if secondary to bone marrow involvement by disease.
   c. Serum aspartate transaminase (AST/SGOT) or alanine transaminase (ALT/SGPT)<3.0× upper limit of normal (ULN).
   d. Serum bilirubin <1.5×ULN unless due to Gilbert's syndrome.
   e. Estimated serum creatinine clearance of ≥60 mL/min using the Cockcroft-Gault equation or directly determined from the 24-hour urine collection method.
9. Agree to scheduled pregnancy testing and Pregnancy Risk Management Plan during the course of the study, and 28 days after the end of study treatment. This applies even if the subject practices true abstinence from heterosexual contact. A female of childbearing potential (FCBP) is a female who: 1) has achieved menarche at some point, 2) has not undergone a hysterectomy or bilateral oophorectomy, or 3) has not been naturally postmenopausal (amenorrhea following cancer therapy does not rule out childbearing potential) for at least 24 consecutive months (i.e., has had menses at any time in the preceding 24 consecutive months) and must:
   a. Have two negative pregnancy tests as verified by the Investigator prior to starting study therapy. Screening pregnancy test (urine or serum) is done at Day −14, Day −1, pre-Cycle 1 Day 1, and a second confirmatory test (serum) is done within 24 hours of Cycle 1 Day 1. In addition, pregnancy test must be done 24 hours prior to Cycle 1 Day 15 prior to administration of Compound 1. She must agree to ongoing pregnancy testing during the course of the study, and after end of study therapy.

This applies even if the subject practices true abstinence from heterosexual contact.
b. Either commit to true abstinence from heterosexual contact (which must be reviewed on a monthly basis and source documented) or agree to use, and be able to comply with, two reliable forms of contraception without interruption as defined in the PPP and provided to the subject at the time of informed consent, 28 days prior to starting Compound 1, during the study therapy (including during dose interruptions), and for 28 days after discontinuation of study therapy or 18 months after last dose of obinutuzumab, whichever is the last.
c. Avoid conceiving for 28 days after the last dose of Compound 1.
d. Agree to abstain from breast feeding while on Compound 1 and for 28 days after its discontinuation.
e. Agree to refrain from donating ova while on Compound 1 for 30 days after its discontinuation.

Male subjects must practice true abstinence (which must be reviewed on a monthly basis) or agree to use a condom (a latex condom is recommended) during sexual contact with a pregnant female or a female of childbearing potential while participating in the study, during dose interruptions and for at least 3 months following investigational product discontinuation, or longer if required for each compound and/or by local regulations, even if he has undergone a successful vasectomy. Males must agree to refrain from donating semen or sperm while on Compound 1 and for 90 days after its discontinuation. (True abstinence is acceptable when this is in line with the preferred and usual lifestyle of the subject. Periodic abstinence (e.g., calendar, ovulation, symptothermal, post-ovulation methods) and withdrawal are not acceptable methods of contraception.)

Exclusion Criteria: The presence of any of the following will exclude a subject from enrollment:
1. Subject has any significant medical condition, laboratory abnormality, or psychiatric illness that would prevent the subject from participating in the study.
2. Subject has any condition including the presence of laboratory abnormalities which places the subject at unacceptable risk if he/she were to participate in the study.
3. Subject has any condition that confounds the ability to interpret data from the study.
4. Prior allogeneic stem cell transplant (SCT)/bone marrow transplant within 12 months of signing the ICF. Subjects who received allogeneic SCT≥12 months before signing the ICF may be eligible provided there is no ongoing graft-versus-host disease (GVHD) and no ongoing immune suppression therapy.
5. Ongoing or active infection requiring parenteral antibiotics.
6. Uncontrolled intercurrent illness including, but not limited to:
a. Chronic symptomatic congestive heart failure (Class III or IV of the New York Heart Association Classification for Heart Disease).
b. Active central nervous system involvement as documented by spinal fluid cytology or imaging.
c. Uncontrolled/active autoimmune hemolytic anemia or thrombocytopenia.
d. Other concurrent severe and/or uncontrolled concomitant medical conditions that could cause unacceptable safety risks or compromise compliance with protocol.
7. Subject has received prior systemic anti-cancer treatment (approved or investigational) ≤5 half-lives or 4 weeks prior to starting Compound 1, whichever is shorter.
8. Subject has received prior CAR-T or other T-cell targeting treatment (approved or investigational)≤4 weeks prior to starting Compound 1.
9. Subject has received prior therapy with CRBN-modulating drug (e.g., lenalidomide, avadomide/CC-122, pomalidomide)≤4 weeks prior to starting Compound 1.
10. History of second malignancies with life expectancy of ≤2 years or requirement of therapy that would confound study results. Such cases should be discussed with medical monitor. This does not include the following:
a. Basal cell carcinoma of the skin.
b. Squamous cell carcinoma of the skin.
c. Carcinoma in situ of the cervix.
d. Carcinoma in situ of the breast.
e. Carcinoma in situ of the bladder.
f. Incidental histologic finding of prostate cancer (Tumor, Node, Metastasis [TNM] TNM stage of T1a or T1b).
11. Known seropositivity for or history of active viral infection with human immunodeficiency virus (HIV), or hepatitis B or C virus (HBV, HCV). Hepatitis B screening is mandatory for all patients (HBsAg and anti-HBc). Patients with active hepatitis B disease should not be treated with obinutuzumab. Patients should be referred to a specialist if they are carriers before treatment starts (see Gazyva PI or Gazyvaro SmPC). Subjects who are positive for anti-HBc and/or anti-HBs but negative for HBsAg and HBV DNA may be treated after consultation with a hepatologist. This does not include false positive result for patients receiving intravenous immunoglobulin (IVIG).
12. Peripheral neuropathy ≥Grade 2.
13. Subject is on chronic systemic immunosuppressive therapy or corticosteroids (e.g., prednisone or equivalent not to exceed 10 mg per day within the last 14 days) or subjects with clinically significant GVHD.
a. Stable use of inhaled corticosteroids is allowed.
b. The use of topical steroids for ongoing skin or ocular GVHD is permitted.
14. History of hypersensitivity to lenalidomide, pomalidomide, thalidomide.
15. Impaired cardiac function or clinically significant cardiac diseases, including any of the following:
a. LVEF<45% as determined by MUGA scan or ECHO.
b. Complete left bundle branch, or bifascicular, block.
c. Congenital long QT syndrome.
d. Persistent or uncontrolled ventricular arrhythmias or atrial fibrillation.
e. QTcF>470 msec on Screening ECG (mean of triplicate recordings).
f. Unstable angina pectoris or myocardial infarction ≤6 months prior to starting Compound 1.
16. Persistent diarrhea or malabsorption ≥NCI CTCAE Grade 2, despite medical management.
17. Active disease transformation (i.e., Richter's Syndrome); subjects with Richter's Syndrome that has resolved >2 years from signing the ICF are eligible.
18. Known acute or chronic pancreatitis.
19. Pregnant or lactating females.
20. Hypersensitivity to obinutuzumab or to any of the excipients.
21. Concurrent administration of strong CYP3A4/5 modulators.

Length of Study: The entire study is expected to last approximately 4 years. The study consists of three phases/periods: Screening, Treatment and Follow-up. During the Screening Phase, lasting up to 28 days from the time of signing informed consent to first dose administered, subjects undergo assessments to determine their eligibility.

Subjects who qualify for enrollment into the study will enter the Treatment Phase, during which subjects receive investigational product(s) [IP(s)] at a predetermined dose and schedule in combination with obinutuzumab until the underlying CLL/SLL has progressed or the subject has discontinued IP treatment for unacceptable toxicity or other reasons.

The Follow-up Phase begins at study treatment discontinuation. Subjects have a visit at the end of treatment as soon as possible once IP has been discontinued and at 28 days after the last dose of IP. All subjects discontinued for any reason other than progressive disease, withdrawal of consent, or death, is contacted every 90 days following the date of the 28-day follow-up visit for information regarding the status of their disease and for the type and start date for any subsequent anticancer therapy. Efficacy assessments (including clinical, laboratory tests, and CT scans) continue until documented PD or initiation of subsequent anti-CLL therapy.

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Study Treatments: Subjects begin treatment upon confirmation of eligibility.

Compound 1 is supplied as capsules for oral administration in appropriate dose strengths. Compound 1 is initiated on Cycle 1 Day 15 at 0.2 mg daily and administered orally for 7 consecutive days followed by 7 days off study drug every 14 days (7/14-day schedule) in each 28-day cycle.

Obinutuzumab is administered as an intravenous infusion. Obinutuzumab is administered on Cycle 1 Days 1, 2, 8, and 15. Obinutuzumab is administered at a dose of 100 mg on Cycle 1 Day 1 and 900 mg on Cycle 1 Day 2 and 1000 mg on each of Cycle 1 Day 8 and Cycle 1 Day 15. The dose of obinutuzumab on Days 1 and 2 of Cycle 1 may be adjusted per institutional practice as long as the combined dose equals 1000 mg. Subjects must receive a full initial dose of 1000 mg obinutuzumab in Cycle 1 at least one week before initiating Compound 1. Obinutuzumab is administered at a dose of 1000 mg on Day 1 of Cycles 2 through 6.

All active and/or ongoing subjects who are receiving clinical benefit in the opinion of the treating investigator may continue to receive study treatment up to a maximum of 24 cycles or 2 years of Compound 1, or until disease progression (PD), unacceptable toxicity, or discontinuation for any other reason, whichever is earlier. In the event Compound 1 is discontinued prior to obinutuzumab, obinutuzumab will also be discontinued. In the event that obinutuzumab is permanently discontinued, Compound 1 may continue. Subjects who achieve minimal residual disease (MRD) negativity (in both peripheral blood and bone marrow) lasting for a minimum of 3 months in duration have the option to discontinue study treatment; study treatment in these subjects may be resumed at the time of MRD positivity.

Overview of Key Efficacy Assessments: Efficacy assessments include 1) overall response rate (ORR) [complete response (CR), complete response with incomplete marrow recovery (CRi), nodular partial response (nPR), partial response (PR), partial response with lymphocytosis (PRL)] as assessed by the iwCLL 2018 guidelines (Tables 1 and 2); 2) clinical laboratory evaluations; 3) tumor imaging assessment (CT scan), 4) one marrow aspirate/biopsy; 5) ECOG Performance status; 6) B-Symptom evaluation.

Overview of Key Safety Assessments: Safety assessments include 1) adverse events (AEs) using the NCI CTCAE v 5 unless otherwise specified for selected AEs; 2) vital signs; 3) physical examination; 4) concomitant medications and procedures; 5) electrocardiogram (ECG); 6) clinical laboratory assessments (including hematology and clinical chemistry with renal and liver function assessment); 7) pregnancy testing; 8) left ventricular ejection fraction (LVEF).

Overview of Pharmacokinetic assessments: Blood samples are collected according to intensive and sparse sampling strategies to characterize Compound 1 PK when administered in combination with obinutuzumab. Obinutuzumab serum concentrations are measured at specified timepoints. Trends in exposure-response relationships of Compound 1 and markers of efficacy, safety, and biological response is also explored. Exposure-response relationships for measures of clinical responses (effectiveness and toxicities) and biomarkers may be explored.

A number of references have been cited, the disclosures of which are incorporated herein by reference in their entirety.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating chronic lymphocytic leukemia/small lymphocytic lymphoma (CLL/SLL), comprising administering to a subject having CLL/SLL a therapeutically effective amount of Compound 3 of the formula:

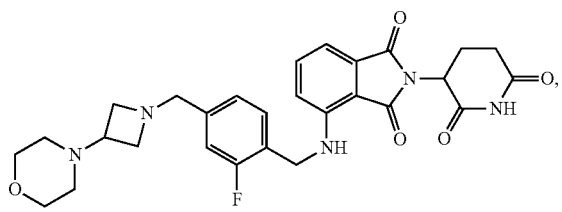

or an enantiomer, mixture of enantiomers, tautomer, isotopolog, or pharmaceutically acceptable salt thereof.

2. A method of treating chronic lymphocytic leukemia/small lymphocytic lymphoma (CLL/SLL), comprising administering to a subject having CLL/SLL a therapeutically effective amount of Compound 1 of the formula:

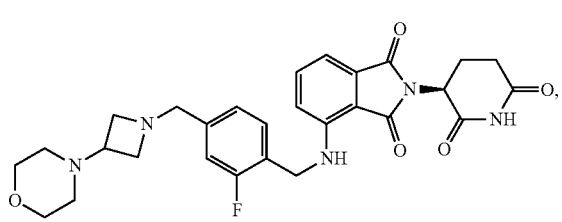

or a tautomer, isotopolog, or pharmaceutically acceptable salt thereof.

3. A method of treating chronic lymphocytic leukemia/small lymphocytic lymphoma (CLL/SLL), comprising administering to a subject having CLL/SLL a therapeutically effective amount of Compound 2 of the formula:

or a tautomer, isotopolog, or pharmaceutically acceptable salt thereof.

4. The method of claim 2, wherein the CLL/SLL is relapsed or refractory CLL/SLL.

5. The method of claim 4, wherein the CLL/SLL is relapsed or refractory to at least two prior therapies.

6. The method of claim 5, wherein at least one of the prior therapies is a Bruton's tyrosine kinase (BTK) inhibitor, a phosphoinositide 3-kinase inhibitor, or venetoclax.

7. The method of claim 6, wherein the BTK inhibitor is ibrutinib, acalabrutinib, zanubrutinib, or tirabrutinib.

8. The method of claim 2, wherein the CLL is newly diagnosed.

9. The method of claim 2, wherein the compound is administered orally.

10. The method of claim 2, wherein the compound is administered once daily for 5 days followed by 2 days of rest.

11. The method of claim 2, wherein the compound is administered once daily for 7 days followed by 7 days of rest.

12. The method of claim 2, wherein the compound is administered once daily for 5 days followed by 9 days of rest.

13. The method of claim 2, wherein the compound is administered once daily for 14 days followed by 14 days of rest.

14. The method of claim 2, wherein the compound is administered once daily for 21 days followed by 7 days of rest.

15. The method of claim 2, wherein the compound is administered on days 1 to 5 of a 7-day cycle, on days 1 to 3 of a 7-day cycle, on days 1 to 5 of a 14-day cycle, on days 1 to 7 of a 14-day cycle, on days 1 to 10 of a 14-day cycle, on days 1 to 7 and days 15 to 21 of a 28-day cycle, on days 1 to 21 of a 28-day cycle, or on days 1 to 14 of a 28-day cycle.

16. The method of claim 2, wherein the compound is administered in an amount of about 0.1 mg, about 0.2 mg, about 0.4 mg, about 0.6 mg, about 0.8 mg, about 1.2 mg or about 1.6 mg per day.

17. The method of claim 2, further comprising administering to the subject a therapeutically effective amount of obinutuzumab.

18. The method of claim 17, wherein obinutuzumab is administered intravenously.

19. The method of claim 18, wherein obinutuzumab is administered at a dose of about 100 mg on day 1 of a first 28-day cycle, about 900 mg on day 2 of the first 28-day cycle, and about 1000 mg on each of days 8 and 15 of the first 28-day cycle and day 1 of a second to a sixth 28-day cycles.

20. The method of claim 17, comprising (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s); and (ii) administering Compound 1 or a pharmaceutically acceptable salt thereof in cycles of once daily for 7 days followed by 7 days of rest, starting on day 15 of Cycle 1.

21. The method of claim 17, comprising (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s); and (ii) administering Compound 1 or a pharmaceutically acceptable salt thereof in cycles of once daily for 5 days followed by 9 days of rest, starting on day 15 of Cycle 1.

22. The method of claim 17, comprising (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s); and (ii) administering Compound 1 or a pharmaceutically acceptable salt thereof in cycles of once daily for 14 days followed by 14 days of rest, starting on day 15 of Cycle 1.

23. The method of claim 17, comprising (i) administering obinutuzumab at a dose of about 100 mg on day 1, about 900 mg on day 2, about 1000 mg on each of days 8 and 15 of the a first 28-day cycle ("Cycle 1"), and at a dose of about 1000 mg on day 1 of the subsequent 28-day cycle(s); and (ii) administering Compound 1 or a pharmaceutically acceptable salt thereof in cycles of once daily for 21 days followed by 7 days of rest, starting on day 15 of Cycle 1.

24. The method of claim 2, comprising administering Compound 1 of the formula:

25. The method of claim 2, comprising administering a pharmaceutically acceptable salt of Compound 1 of the formula:

* * * * *

UNITED STATES PATENT AND TRADEMARK OFFICE
CERTIFICATE OF CORRECTION

| | |
|---|---|
| PATENT NO. | : 11,628,172 B2 |
| APPLICATION NO. | : 17/075125 |
| DATED | : April 18, 2023 |
| INVENTOR(S) | : Janardhanan et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 127 days.

Signed and Sealed this
Fourth Day of March, 2025

Coke Morgan Stewart
*Acting Director of the United States Patent and Trademark Office*